(12) United States Patent
Dieterle et al.

(10) Patent No.: US 7,396,956 B2
(45) Date of Patent: Jul. 8, 2008

(54) PROCESS FOR STABLY OPERATING A CONTINUOUS PREPARATION PROCESS FOR OBTAINING ACROLEIN OR ACRYLIC ACID OR A MIXTURE THEREOF FROM PROPANE

(75) Inventors: Martin Dieterle, Mannheim (DE); Götz-Peter Schindler, Ludwigshafen (DE); Catharina Klanner, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/555,474

(22) Filed: Nov. 1, 2006

(65) Prior Publication Data

US 2007/0123732 A1    May 31, 2007

Related U.S. Application Data

(60) Provisional application No. 60/732,658, filed on Nov. 3, 2005.

(30) Foreign Application Priority Data

Nov. 3, 2005  (DE) .................. 10 2005 052 923

(51) Int. Cl.
   *C07C 45/00*    (2006.01)
(52) U.S. Cl. .................................................. 562/545
(58) Field of Classification Search .................. None
   See application file for complete search history.

(56) References Cited

U.S. PATENT DOCUMENTS

| | | | |
|---|---|---|---|
| 32,082 A | 4/1861 | Rice | |
| 3,161,670 A | 12/1964 | Adams et al. | |
| 4,413,147 A | 11/1983 | Khoobiar | |
| 4,532,365 A | 7/1985 | Khoobiar | |
| 4,535,188 A | 8/1985 | Khoobiar | |
| 6,781,017 B2 | 8/2004 | Machhammer et al. | |
| 6,858,754 B2 | 2/2005 | Borgmeier | |
| 6,867,328 B2 | 3/2005 | Borgmeier et al. | |
| 7,005,403 B2 | 2/2006 | Borgmeier et al. | |
| 7,026,506 B2 | 4/2006 | Borgmeier et al. | |
| 7,115,775 B2 * | 10/2006 | Buschulte et al. ........... 562/544 |
| 7,214,822 B2 | 5/2007 | Borgmeier et al. | |
| 7,238,827 B2 | 7/2007 | Hechler et al. | |
| 2003/0181762 A1 | 9/2003 | Machhammer et al. | |
| 2003/0187298 A1 | 10/2003 | Borgmeier et al. | |
| 2003/0187299 A1 | 10/2003 | Machhammer et al. | |
| 2004/0063988 A1 | 4/2004 | Hechler et al. | |
| 2004/0082810 A1 | 4/2004 | Borgmeier et al. | |
| 2004/0102648 A1 | 5/2004 | Borgmeier et al. | |
| 2004/0116741 A1 | 6/2004 | Nordhoff et al. | |
| 2004/0138499 A1 * | 7/2004 | Buschulte et al. ........... 562/545 |
| 2004/0138500 A1 | 7/2004 | Borgmeier | |
| 2004/0199001 A1 | 10/2004 | Schindler et al. | |
| 2005/0119515 A1 | 6/2005 | Machhammer et al. | |
| 2005/0222459 A1 | 10/2005 | Nordhoff et al. | |
| 2006/0004226 A1 | 1/2006 | Machhammer et al. | |
| 2006/0004227 A1 | 1/2006 | Dieterle et al. | |
| 2006/0004229 A1 | 1/2006 | Dieterle et al. | |
| 2006/0074258 A1 | 4/2006 | Borgmeier et al. | |
| 2006/0183940 A1 * | 8/2006 | Buschulte et al. ........... 562/545 |
| 2006/0258529 A1 | 11/2006 | Diefenbacher et al. | |
| 2007/0088092 A1 | 4/2007 | Klanner et al. | |

FOREIGN PATENT DOCUMENTS

| | | |
|---|---|---|
| DE | 33 13 573 A1 | 10/1983 |
| DE | 102 11 275 A1 | 9/2003 |
| DE | 102 45 585 A1 | 4/2004 |
| DE | 102 46 119 A1 | 4/2004 |
| DE | 103 16 039 A1 | 10/2004 |
| DE | 10 2004 032 129 A1 | 3/2005 |
| DE | 10 2005 009 885 A1 | 9/2006 |
| DE | 10 2005 009 891 A1 | 9/2006 |
| DE | 10 2005 010 111 A1 | 9/2006 |
| DE | 10 2005 013 039 A1 | 9/2006 |
| DE | 10 2005 022 798 A1 | 11/2006 |
| DE | 10 2005 049 699 A1 | 4/2007 |
| EP | 0 117 146 A1 | 8/1984 |
| EP | 0 799 169 B1 | 3/2000 |
| WO | WO 01/96270 A2 | 12/2001 |
| WO | WO 02/055469 A1 | 7/2002 |
| WO | WO 03/078378 A1 | 9/2003 |

* cited by examiner

*Primary Examiner*—Yvonne Eyler
*Assistant Examiner*—M Louisa Lao
(74) *Attorney, Agent, or Firm*—Oblon, Spivak, McClelland, Maier & Neustadt, P.C.

(57) ABSTRACT

A process for stably operating a continuous preparation process for obtaining acrolein or acrylic acid or a mixture thereof from propane, in which the feed rate of fresh propane to the process is utilized as a correcting element for stable steady-state operation.

14 Claims, 1 Drawing Sheet

PROCESS FOR STABLY OPERATING A CONTINUOUS PREPARATION PROCESS FOR OBTAINING ACROLEIN OR ACRYLIC ACID OR A MIXTURE THEREOF FROM PROPANE

The present invention relates to a process for stably operating a continuous preparation process for obtaining acrolein or acrylic acid or a mixture thereof from propane, in which A) in a first reaction zone A, propane is subjected in the presence of molecular oxygen to a heterogeneously catalyzed dehydrogenation to obtain a product gas mixture A comprising propane and propylene, B) if appropriate, product gas mixture A is conducted into a first separation zone A in order to remove a portion or more of constituents other than propane and propylene present in product gas mixture A therefrom and thus to obtain a remaining product gas mixture A' comprising propane and propylene, C) product gas mixture A or product gas mixture A' is used in a second reaction zone B to charge at least one oxidation reactor and, in the at least one oxidation reactor, propylene present in product gas mixture A or in product gas mixture A' is subjected to a selective heterogeneously catalyzed partial gas phase oxidation with molecular oxygen to give a product gas mixture B comprising acrolein or acrylic acid or a mixture thereof as the target product, unconverted propane, excess molecular oxygen and any unconverted propylene, D) in a second separation zone B, target product present in product gas mixture B is removed and, from the remaining residual gas comprising propane, molecular oxygen and any unconverted propylene, at least a portion comprising unconverted propane, molecular oxygen and any unconverted propylene is recycled as cycle gas 1 comprising molecular oxygen into reaction zone A in cycle gas mode, E) fresh propane is fed to the continuous preparation process via at least one of the zones from the group comprising reaction zone A, separation zone A, reaction zone B and separation zone B at a feed rate which has a predefined steady-state value in the stable operating state of the preparation process, and F) the content of molecular oxygen in product gas mixture B is determined continuously and compared to the steady-state target content of molecular oxygen in product gas mixture B predefined for the stable operating state of the preparation process.

As a partial oxidation product of propylene, acrylic acid is a significant monomer which finds use as such or in the form of its alkyl esters for obtaining, for example, polymers suitable as adhesives or water-superabsorbing polymers (cf., for example, WO 02/055469 and WO 03/078378). Acrolein is a significant intermediate, for example for the preparation of glutaraldehyde, methionine, folic acid and acrylic acid.

In contrast to the exothermic heterogeneously catalyzed oxydehydrogenation of propane, which is forced by oxygen present and in which free hydrogen is neither formed as an intermediate (the hydrogen pulled from the propane to be dehydrogenated is pulled out directly as water ($H_2O$)) nor is detectable, a heterogeneously catalyzed dehydrogenation shall be understood in this document to mean a (conventional) dehydrogenation whose thermal character, in contrast to the oxydehydrogenation, is endothermic (an exothermal hydrogen combustion may be included in the heterogeneously catalyzed dehydrogenation in the first reaction zone A as a subsequent step) and in which free molecular hydrogen is formed at least as an intermediate. This generally requires different reaction conditions and different catalysts than the oxydehydrogenation.

In a corresponding manner, fresh propane in this document is understood to mean propane which has participated neither in a dehydrogenation in reaction zone A nor in a partial oxidation of propylene to acrolein and/or acrylic acid in reaction zone B. It has preferably not participated in any chemical reaction at all. In general, it is supplied in the form of crude propane which preferably fulfills the specification according to DE-A 102 46 119 or of DE-A 102 45 585, and which normally also comprises components other than propane in small amounts. Such crude propane is obtainable, for example, by processes described in DE-A 10 2005 022 798. Normally crude propane comprises propane to an extent of at least ≧90% by weight and preferably to an extent of at least ≧95% by weight.

In this document, inert gas shall be understood quite generally to mean a reaction gas constituent which behaves substantially inertly under the conditions of the appropriate reaction and, each inert reaction gas constituent taken alone, remains chemically unchanged to an extent of more than 95 mol %, preferably to an extent of more than 98 mol % and more preferably to an extent of more than 99 mol %. Examples of such inert gases in reaction zones A and B are $N_2$, noble gases, $CO_2$ or else steam.

In this document, the loading of a catalyst bed catalyzing one reaction step with reaction gas mixture is understood to mean the amount of reaction mixture in standard liters (=l (STP); the volume in liters that the appropriate amount of reaction gas mixture would take up under standard conditions (0° C., 1 bar)) which is conducted through one liter of catalyst bed (e.g. fixed catalyst bed) per hour. However, the loading may also be based only on a constituent of the reaction gas mixture. In that case, it is the amount of this constituent in l (STP)/l·h which is conducted through one liter of catalyst bed per hour (pure inert material beds are not counted in the fixed catalyst bed). The loading may also be based only on the amount of catalyst present in one catalyst bed which may comprise the actual catalyst diluted with inert material (in that case, this is stated explicitly).

Processes for preparing acrolein and/or acrylic acid, in which the propylene is obtained from propane by partial heterogeneously catalyzed dehydrogenation and, in the presence of unconverted (inert) propane, subjected as a constituent of a partial oxidation mixture to a heterogeneously catalyzed partial gas phase oxidation with molecular oxygen to give product mixtures comprising acrolein and/or acrylic acid, are known (cf., for example, DE-A 10 2005 022 798, DE-A 102 46 119, DE-A 102 45 585, DE-A 10 2005 049 699, DE-A 10 2004 032 129, DE-A 10 2005 013 039, DE-A 10 2005 010 111, DE-A 10 2005 009 891, DE-A 102 11 275, EP-A 117 146, U.S. Pat. No. 3,161,670, DE-A 33 13 573, WO 01/96270, DE-A 103 16 039, DE-A 10 2005 009 885 and the prior art cited in this document).

It is also known from the aforementioned prior art that it is favorable with a view to the lifetime of the catalysts used when product gas mixture B in the partial oxidation still comprises unconverted molecular residual oxygen.

However, it is also known that the target product removal in separation zone B is generally accompanied by at least incomplete separation, if any, of molecular oxygen and propane present in product gas mixture B. As a result, cycle gas 1 likewise comprises molecular oxygen which normally causes partial full combustion of propane and propylene in reaction zone A, which influences both the selectivity of propylene formation and the thermal balance in reaction zone A.

A stable operation, designed for long-term production, of a continuous preparation process as described at the outset for obtaining acrolein or acrylic acid or a mixture thereof therefore has the prerequisite of a stable oxygen content of product gas mixture B. Depending on the catalysts and reaction and process conditions used in reaction zones A and B, the aforementioned (target) oxygen content of product gas mixture B in the steady operating state of the preparation process may, for example, be from 0.1 to 6% by volume, preferably from 0.5 to 5% by volume and more preferably from 1.5 to 4% by volume, for example also 3% by volume. The steady-state "value" of the oxygen content in product gas mixture B predefined for the steady-state operation of the preparation process may also be an interval (e.g. ±0.3% by volume, or ±0.2% by volume, or ±0.1% by volume) around a mean value (for example 3±0.1% by volume; in this case, regulation would be effected only when the current time value leaves the interval around the mean value).

In-depth investigations of the steady-state operation of a preparation process practiced as described has shown that the oxygen content of product gas mixture B in practice frequently deviates temporarily from the predefined (desired) stationary value (the target content) as a guide parameter (regulating parameter) without there being any deviation in the feed rate of molecular oxygen for reaction zone B from its ideal value (steady-state value).

Such deviations are typically comparatively restricted and generally caused by slight deviations in various elements of the overall process from the ideal line. Typically, they vary within a deviation range of in some cases ±20%, in many cases ±10%, frequently ±5%, or ±3%, based in each case on the steady-state target content (or the mean value of the steady-state target content interval). The deviations leaving the aforementioned range are generally disruptions to the oxygen feed to the overall process (or other larger disruptions) which then have to be eliminated by immediate change thereof.

For deviations within the range mentioned, a suitable other correcting element which counteracts the deviation of the oxygen content in product gas mixture B from the predefined steady-state value and returns the preparation process to the steady operating state (i.e. prevents the process from running further away from the steady state at an early stage) is required. It is essential that the correcting element does not react too slowly. In-house investigations have, for example, shown that, for example, changes of reaction temperatures which influence the oxygen consumption in the preparation process generally react relatively slowly as correcting elements, since both the supply and the withdrawal of heat into and from the preparation process proceed relatively slowly owing to the comparatively finite heat transfer numbers.

It was therefore an object of the present invention to provide a process for stably operating a continuous preparation process as described at the outset for obtaining acrolein or acrylic acid or a mixture thereof from propane with a suitable correcting element for the content of molecular oxygen in product gas mixture B as a control parameter.

Accordingly, a process has been found for stably operating a continuous preparation process for obtaining acrolein or acrylic acid or a mixture thereof from propane, in which A) in a first reaction zone A, propane is subjected in the presence of molecular oxygen to a heterogeneously catalyzed dehydrogenation to obtain a product gas mixture A comprising propane and propylene, B) if appropriate, product gas mixture A is conducted into a first separation zone A in order to remove a portion or more of constituents other than propane and propylene present in product gas mixture A therefrom and thus to obtain a remaining product gas mixture A' comprising propane and propylene, C) product gas mixture A or product gas mixture A' is used in a second reaction zone B to charge at least one oxidation reactor and, in the at least one oxidation reactor, propylene present in product gas mixture A or in product gas mixture A' is subjected to a selective heterogeneously catalyzed partial gas phase oxidation with molecular oxygen to give a product gas mixture B comprising acrolein or acrylic acid or a mixture thereof as the target product, unconverted propane, excess molecular oxygen and any unconverted propylene, D) in a second separation zone B, target product present in product gas mixture B is removed and, from the remaining residual gas comprising propane, molecular oxygen and any unconverted propylene, at least a portion comprising unconverted propane, molecular oxygen and any unconverted propylene is recycled as cycle gas 1 comprising molecular oxygen into reaction zone A in cycle gas mode, E) fresh propane is fed to the continuous preparation process via at least one of the zones from the group comprising reaction zone A, separation zone A, reaction zone B and separation zone B at a feed rate which has a predefined steady-state value in the stable operating state of the preparation process, and F) the content of molecular oxygen in product gas mixture B is determined continuously and compared to the steady-state target content of molecular oxygen in product gas mixture B predefined for the stable operating state of the preparation process, wherein in the case that the content of molecular oxygen determined at one time in product gas mixture B is greater than the steady-state target content, after this time, fresh propane is fed to the preparation process at a feed rate (the feed rate of the fresh propane is the correcting element selected in accordance with the invention) which is greater than its steady-state value, and in the case that the content of molecular oxygen determined at one time in product gas mixture B is less than the steady-state target content, after this time, fresh propane is fed to the preparation process at a feed rate which is less than its steady-state value.

Apart from the characterizing part, the process according to the invention may be carried out like the preparation processes described in the documents EP-A 799 169, U.S. Pat. No. 4,788,371, U.S. Pat. No. 6,566,573, DE-A 10 2005 022 798, DE-A 102 46 119, DE-A 102 45 585, DE-A 10 2005 049 699, DE-A 10 2004 032 129, DE-A-10 2005 013 039, DE-A 10 2005 010111, DE-A 10 2005 009 891, DE-A 102 11 275, EP-A 117 146, U.S. Pat. No. 3,161,670, DE-A 33 13 573, WO 01/96270, DE-A 103 16 039, DE-A 10 2005 009 885 and the prior art cited in these documents.

In the process according to the invention, the feed rate of fresh propane is understood to mean that amount of propane which is fed freshly (i.e. without having taken part beforehand in a dehydrogenation in reaction zone A or in a partial oxidation in reaction zone B (more preferably, it has not taken part in any chemical reaction at all beforehand)) overall to the preparation process per time unit. The advantage of the feed rate of fresh propane as the correcting element selected in accordance with the invention is that, as a consequence of the high flow rate of the reaction gases within the preparation process, a rapid return of the preparation process to the steady operating state is thus ensured. The return principle is based on an increased feed rate of fresh propane being accompanied under otherwise substantially unchanged preparation process conditions by a comparatively increased formation rate of propylene in reaction zone A. This results in an increased propylene feed rate into reaction zone A which leads the oxygen content increased in product gas mixture B in comparison to the steady operating state, by appropriate reaction with molecular oxygen in reaction zone B, back toward the steady-state target content predefined for the preparation process. Conversely, a reduced feed rate of fresh propane, under otherwise substantially unchanged preparation process conditions, is accompanied by a comparatively reduced formation rate of propylene in reaction zone A. This results in a reduced (compared to the steady operating state) propylene feed rate into reaction zone B which leads the oxygen content reduced in product gas mixture B in comparison to the steady operating state, by reaction with molecular oxygen proceeding correspondingly to a reduced extent in reaction zone B, back toward the steady-state target content predefined for the preparation process. In addition, a changed propylene formation rate in reaction zone A is accompanied by changed endothermicity of the propylene formation therein, which is capable of leveling out a combustion exothermicity changed by the changed $O_2$ content in reaction zone A therein (this advantage arises especially when the feed rate of fresh propane is changed directly into reaction zone A; this is the case in particular when it is changed directly into the reaction gas mixture input gas fed to reaction zone A). Moreover, in reaction zone A, any accompanying changes in the reaction temperature in reaction zone A may, if required, be corrected by appropriate change in the temperature, for example of the gases fed to reaction zone A. The changed feed rate of fresh propane is maintained in the process according to the invention generally until the deviation in the content of molecular oxygen in product gas mixture B from the target content begins to change its preceding sign, etc.

Another advantage of the feed rate of fresh propane as the correcting element selected in accordance with the invention is that a change in it is accompanied merely by a comparatively restricted change in the total reaction gas flow rate. This is caused by a feed of fresh propane not necessarily being accompanied by a significant feed of components other than fresh propane. This would be the case, for example, if a changed residual oxygen content in reaction zone B were to be countered by varying air metering directly into reaction zone A, since atmospheric oxygen is always accompanied by four times the molar amount of nitrogen. However, the provision of pure molecular oxygen (as an alternative correcting element) is comparatively costly and inconvenient.

The aforementioned is true in particular when the predefined steady-state target content in the product gas mixture B of molecular oxygen is predefined in % by volume and based on the total volume of product gas mixture B.

However, it is also true when the predefined steady-state target content in product gas mixture B of molecular oxygen is predefined in % by weight and based on the total weight of product gas mixture B.

The content of molecular oxygen in product gas mixture B can be determined in a wide variety of different ways. According to the invention, it is preferably effected online. For example, the method disclosed in DE-A 101 17 678 can be employed, which is based on obtaining a signal which is correlated with the oxygen content of product gas mixture B. For example, the signal can be obtained by passing electromagnetic radiation having a wavelength $\lambda_o$ (for example within the IR region) at which molecular oxygen absorbs electromagnetic radiation (for example from 759.5 to 768 nm) through (the) product gas mixture B, and measuring the unabsorbed fraction of the electromagnetic radiation. For example, the oxygen content of product gas mixture B can be measured by means of a laser beam whose wavelength is adjusted to one of the rotational fine structure bands of molecular oxygen. To calibrate the measurement of the oxygen content, the laser beam can radiate through a calibration cell which comprises a gas (for example product gas mixture B in the steady state) with a defined oxygen content, or through which a gas with a defined oxygen content is passed. For example, the aforementioned laser may be a diode laser whose wavelength is adjustable to one of the rotational fine structure bands of molecular oxygen in the range from 759.5 nm to 768 nm. The modulation range may be ±0.05 nm. In principle, the measurement can be carried out directly, for example through an appropriate window, in product gas mixture B itself. However, it is also possible to branch off a small stream of product gas mixture B (with the same composition) via a bypass for said measurement, as described and recommended, for example, in DE-A 101 17 678.

In principle, for the purpose described, it is possible, for example, to use an Ultramat® 23 gas analysis unit from Siemens (works in the IR region). Useful units are, for example, 7MB2335, 7MB2337 and 7MB2338 (cf. the brochure "Siemens, Ultramat 23, Betriebsanleitung, Bestell-Nr.: C79000-B5200-C216-02, Version 01/2005").

However, also suitable for the process according to the invention are measurement processes and units which are based on the comparatively great paramagnetic susceptibility of molecular oxygen, for example oxygen analyzers of the PMA® range from M&C Products Analysentechnik GmbH in D-40885 Ratingen. These are analytical units which are particularly advantageous owing to their very rapid response time, their low dead volume, their low cross-sensitivity with respect to other gas constituents and also the direct flow through the measurement cell (for example the version PMA 30). The measurement process based on the aforementioned principle is one of the most precise quantitative determination processes for oxygen in the range from 0 to 100% by volume. In the aforementioned units, a diamagnetic dumb-bell with a mirror disposed at the center of rotation is secured to tensioning bands and mounted in an inhomogeneous magnetic field. Owing to its paramagnetism, the oxygen attempts to reach the inhomogeneous magnetic field of the measurement cell. The $O_2$ molecules exert a torque on the dumb-bell and deflect it. Optical scanning generates a current electronically, which flows through a wire loop which is laid around the dumb-bell and turns it back to the neutral position. The compensation current is proportional to the oxygen content of the measurement gas, as a result of which the $O_2$ indication is absolutely linear.

However, useful $O_2$ determination methods for the process according to the invention in principle also include gas chromatography methods or electrochemistry methods. In the latter, the molecular oxygen is ionized, for example, by a suitable energy supply and the electrical conductivity of the gas is subsequently determined.

As already mentioned, the steady-state target content of molecular oxygen in product gas mixture B in the process according to the invention may be set, for example, to from 0.1 to 6% by volume, preferably to from 0.5 to 5% by volume, more preferably to from 1.5 to 4% by volume and, for example, also to 3% by volume. However, the aforementioned setting can also extend to from 0.1 to 6% by weight, or from 0.5 to 5% by weight, or from 1.5 to 4% by weight, or, for example, also 3% by weight.

When the actual oxygen content of product gas mixture B deviates from the predefined steady-state target content, the feed rate of fresh propane is adjusted appropriately in accordance with the invention. According to the invention, the adjustment is appropriately effected such that the resulting changed propylene formation rate in reaction zone A is such that the oxygen content deviation in reaction zone B, based on the partial oxidation in the steady state, is essentially just compensated in each case by a deviation in propylene content equivalent in reaction stoichiometry.

In principle, it is possible in the process according to the invention for the fresh propane required for the preparation process to be fed via each of the zones from the group comprising reaction zone A, separation zone A, reaction zone B and separation zone B. This is true in particular when cycle gas 1 comprises the entire amount of the residual gas which remains in separation zone B and comprises propane and molecular oxygen, and also any propylene.

Advantageously, the fresh propane is fed for the preparation process of the process according to the invention exclusively into reaction zone A (this generally causes the highest target product selectivities based on propane fed). However, it can also be fed into any other of the different zones and also simultaneously via more than one zone (in particular, a feed of fresh propane directly upstream of reaction zone B may, for example, be appropriate when this brings about stabilization of the explosion behavior of the reaction gas mixture in the partial oxidation zone (reaction zone B)). In a corresponding manner, the inventive change in the feed rate of fresh propane in the process according to the invention can be effected into any of the zones.

When the fresh propane is fed for the preparation process of the process according to the invention exclusively into reaction zone A, the inventive change in the feed rate of fresh propane is, in accordance with the invention, also appropriately undertaken exclusively into reaction zone A, i.e. at the same feed point. Otherwise (as already mentioned), it is generally advantageous to undertake the change in the feed rate of fresh propane into reaction zone A.

Moreover, the preparation process underlying the process according to the invention can, as already mentioned, be performed as described in the documents of the acknowledged prior art.

In this connection, it has been proposed in the documents DE-A 10 2004 032 129 and DE-A 10 2005 013 039 that a mixture of steam, fresh propane and cycle gas 1 be fed as reaction gas mixture input gas to reaction zone A for the purpose of the partial heterogeneously catalyzed dehydrogenation of the propane present in the reaction gas mixture input gas to propylene. The heterogeneously catalyzed propane dehydrogenation should appropriately be implemented in the form of a tray reactor in which the catalyst beds are favorably arranged in radial or axial succession. Appropriately, in such a tray reactor, the fixed catalyst bed type is employed.

Advantageously, the number of catalyst bed trays in such a tray reactor is three. The prior art recommends performing the heterogeneously catalyzed partial propane dehydrogenation autothermally. To this end, molecular oxygen (for example in the form of air) is added to a restricted extent to the reaction gas mixture beyond the first catalyst bed passed through and between the (fixed) catalyst beds which follow the first (fixed) catalyst bed in flow direction. For example, generally catalyzed by the dehydrogenation catalysts themselves, restricted combustion of hydrogen formed in the course of the heterogeneously catalyzed propane dehydrogenation (and also, if appropriate, of propane and/or propylene to a minor extent at most) can be brought about, whose exothermicity substantially retains the dehydrogenation temperature (adiabatic reactor configuration).

In comparative examples 1, 3 and 4 of DE-A 10 2004 032 129 and in the working example of DE-A 10 2005 010 111, a heterogeneously catalyzed partial propane dehydrogenation as described above is simulated in a tray reactor (3 catalyst bed trays) by three dehydrogenation reactors connected in series. Instead of such a series connection of tubular reactors, it is also possible in these comparative examples or in this working example to use a tray reactor according to the remarks of DE-A 10 2005 049 699.

The catalyst to be used in each case is the catalyst of the corresponding comparative example or of the working example. The same applies to the reaction temperatures and the composition of the reaction gas mixture input gas.

Appropriately, the partial heterogeneously catalyzed dehydrogenation of propane is substantially operated, divided between the three catalyst trays, in such a way that the conversion of the propane conducted into the reactor, based on single reactor pass, is approx. 20 mol %. The selectivity of propylene formation achieved is regularly 90 mol %. The maximum contribution of a single tray to the conversion migrates from the front backward in flow direction with increasing operating time. In general, the catalyst charge is regenerated before the third tray in flow direction provides the maximum contribution to the conversion. Advantageously, the regeneration is effected when the carbonization of all trays has attained an identical extent.

It is quite generally favorable for the above-described heterogeneously catalyzed partial dehydrogenation of propane when the loading on the total amount of catalyst (sum over all beds) with the total amount of propane and propylene is $\geq 500$ I (STP)/I·h and $\leq 20\,000$ I (STP)/I·h (typical values are from 1500 I (STP)/I·h to 2500 I (STP)/I·h). The maximum reaction temperature within an individual fixed catalyst bed is advantageously kept at from 500° C. to 600° C. (or to 650° C.). Particularly advantageously, the reaction gas mixture input gas in the above-described heterogeneously catalyzed partial propane dehydrogenation stage in the tray reactor consists merely of fresh propane and the cycle gas 1 which has been recycled from the partial oxidation into the dehydrogenation and, stemming from the partial oxidation, comprises a sufficient amount of steam to result in a satisfactory lifetime of the dehydrogenation catalyst beds. In other words, the comparative examples and the example can be carried out in this way in the tray reactors described even when the addition of the extra steam in the dehydrogenation is dispensed with. Otherwise, the statements made on such procedures in DE-A 10 2005 009 885, DE-A 10 2005 010 111, DE-A 10 2005 049 699, DE-A 10 2005 009 891, DE-A 10 2005 013 039 and DE-A 10 2004 032 129 apply.

A disadvantage of the prior art process described is that virtually all catalysts which catalyze the dehydrogenation of propane also catalyze the combustion (full oxidation of propane and propylene to carbon oxides and steam) of propane and propylene with molecular oxygen, and, as already stated, molecular oxygen is present in the cycle gas 1 from the partial oxidation which is recycled into the heterogeneously catalyzed partial dehydrogenation of propane.

It has therefore already been proposed (see DE-A 102 11 275), in an inventive preparation of acrolein and/or acrylic acid from propane, to perform the heterogeneously catalyzed partial propane dehydrogenation in such a way that the product gas withdrawn from the dehydrogenation zone is divided into two portions of identical composition in order to feed only one of the two portions as product gas mixture A, or, if appropriate, as product gas mixture A' after performance of a secondary component removal, to the partial oxidation, while the other portion is recycled into the dehydrogenation as a constituent of the reaction gas mixture input gas. The molecular hydrogen present in this cycle gas coming from the dehydrogenation itself is then intended to protect the propane and, if appropriate, propylene present in the reaction gas mixture input gas from the molecular oxygen which is likewise present in this input gas. This protection is based on the fact that the combustion, normally catalyzed heterogeneously by the same catalysts, of molecular hydrogen to water is preferred kinetically over the full combustion of propane and/or propylene.

DE-A 102 11 275 recommends the conduction of dehydrogenation cycle gas by the jet pump principle (it is also referred to as loop mode). This document also addresses the possibility of adding molecular hydrogen additionally to the reaction gas mixture in the propane dehydrogenation. DE-A 10 2005 049 699 makes an appropriate statement on the requirement to meter the molecular hydrogen into the motive jet for the jet pump in a certain feed hierarchy.

DE-A 10 2004 032 129 and DE-A 10 2005 013 039 propose not undertaking the recycling of the cycle gas 1 which comprises molecular oxygen and stems from the heterogeneously catalyzed partial oxidation into the reaction gas mixture input gas for the heterogeneously catalyzed partial propane dehydrogenation. Instead, the recycling into the reaction gas mixture of the dehydrogenation should not be effected until after a certain dehydrogenation conversion. DE-A 10 2004 032 129 also proposes adding external molecular hydrogen additionally to the reaction gas mixture of the dehydrogenation prior to this recycling. In addition, DE-A 10 2004 032 129 also propagates the loop mode for the dehydrogenation. !n this case, motive jet is exclusively the cycle gas recycled from the partial oxidation into the dehydrogenation.

Against this background, DE-A 10 2005 009 885 recommends, in working example 11, a loop mode in which the reaction gas mixture input gas for the heterogeneously catalyzed partial dehydrogenation of propane is composed of cycle gas 1 which is recycled from the partial oxidation and is composed of fresh propane, of external molecular hydrogen, of a minimum amount of external steam and cycle gas recycled from the dehydrogenation itself (it would also be possible to dispense with the external steam). The motive jet used is a mixture of fresh propane, external molecular hydrogen, cycle gas 1 from the partial oxidation and external steam. With regard to any metering sequence to be observed in generating the motive jet, DE-A 10 2005 009 885 makes no statement. Recommendations on this subject are given by DE-A 10 2005 049 699.

Useful dehydrogenation catalysts for reaction zone A of the process according to the invention are in principle all dehydrogenation catalysts known in the prior art. They can be divided roughly into two groups, specifically into those which are of oxidic nature (for example chromium oxide and/or aluminum oxide) and into those which consist of at least one generally comparatively noble metal (for example platinum) deposited on a generally oxidic support. The dehydrogenation catalysts which may be used thus include all of those recommended in WO 01/96270, EP-A 731 077, DE-A 10211275, DE-A 10131297, WO 99/46039, U.S. Pat. No. 4,788,371, EP A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105, U.S. Pat. No. 3,670,044, U.S. Pat. No. 6,566,573, U.S. Pat. No. 4,788,371, WO-A 94/29021 and DE-A 199 37 107. In particular, the catalyst according to Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the Periodic Table of the Elements, lanthanum and/or tin, with the proviso that the sum of the percentages by weight adds up to 100% by weight.

Also particularly suitable is the dehydrogenation catalyst used in the example of this document.

Generally, the dehydrogenation catalysts may be catalyst extrudates (diameter typically from 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). For a heterogeneously catalyzed dehydrogenation in a fluidized bed (or moving bed), more finely divided catalyst will accordingly be used. Preference is given in accordance with the invention to the fixed catalyst bed for reaction zone A.

In general, the dehydrogenation catalysts (especially those used by way of example in this document and those recommended in DE-A 19937107 (especially the exemplary catalysts of this DE-A)) are such that they are capable of catalyzing both the dehydrogenation of propane and the combustion of propane and of molecular hydrogen. The combustion of hydrogen proceeds very much more rapidly over the catalysts both in comparison to the dehydrogenation of propane and in comparison to its combustion in the case of a competition situation.

In addition, all reactor types and process variants known in the prior art are useful in principle for the heterogeneously catalyzed propane dehydrogenation in reaction zone A. Descriptions of such process variants are present, for example, in all prior art documents cited with regard to the dehydrogenation catalysts and the prior art cited at the outset of this document.

A comparatively comprehensive description of dehydrogenation processes suitable in accordance with the invention for reaction zone A is also present in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

It is characteristic of the partial heterogeneously catalyzed dehydrogenation of propane that it proceeds endothermically. This means that the heat (energy) required for the attainment of the required reaction temperature has to be supplied to the starting reaction gas mixture (the reaction gas mixture input gas) either beforehand and/or in the course of the heterogeneously catalyzed dehydrogenation.

In other words, based on single pass of the charge gas mixture fed to reaction zone A (reaction gas mixture input gas) through reaction zone A, reaction zone A can be configured isothermally by virtue of controlled heat exchange with (fluid, i.e. liquid or gaseous) heat carriers conducted outside reaction zone A.

However, with the same reference basis, it can also be designed adiabatically, i.e. substantially without such a controlled heat exchange with heat carriers conducted outside reaction zone A. In the latter case, the gross thermal character, based on single pass of the starting reaction gas mixture fed to reaction zone A through reaction zone A, by taking measures which have been recommended in the above documents (acknowledged in the prior art) and are yet to be described below, may be configured endothermically (negative) or autothermally (essentially zero) or exothermically (positive).

Typically, the heterogeneously catalyzed partial dehydrogenation of propane to propylene requires comparatively high reaction temperatures. The achievable conversion is normally restricted by the thermodynamic equilibrium. Typical reaction temperatures are from 300 to 800° C. or from 400 to 700° C. One molecule of hydrogen is obtained per molecule of propane to be dehydrogenated to propylene.

High temperatures and removal of the $H_2$ reaction product shift the equilibrium position toward the target product, as does partial pressure reduction by inert dilution.

In addition, it is typical of heterogeneously catalyzed dehydrogenations of propane in particular, owing to the high reaction temperatures required, that small amounts of high molecular weight organic compounds having a high boiling point, up to and including carbon, are formed and are deposited on the catalyst surface, thus deactivating it. In order to minimize this disadvantageous accompanying phenomenon, the propane-containing reaction gas mixture which is to be passed at elevated temperature over the catalyst surface for the heterogeneously catalyzed dehydrogenation can be diluted with steam. Carbon which is deposited is partly or fully eliminated under the resulting conditions by the principle of coal gasification.

Another means of eliminated deposited carbon compounds is to allow a gas comprising oxygen to flow through the dehydrogenation catalyst at elevated temperature from time to time and thus to effectively burn off the deposited carbon. However, substantial suppression of the formation of carbon deposits is also possible by adding molecular hydrogen to the propane to be dehydrogenated under heterogeneous catalysis before it is conducted over the dehydrogenation catalyst at elevated temperature.

There is of course also the possibility of adding a mixture of steam and molecular hydrogen to the propane to be dehydrogenated under heterogeneous catalysis. An addition of molecular hydrogen to the heterogeneously catalyzed dehydrogenation of propane also reduces the undesired formation of allene (propadiene), propyne and acetylene as by-products.

It may therefore be appropriate in accordance with the invention (as already addressed) to carry out the propane dehydrogenation (for example with comparatively low propane conversion) (quasi-)adiabatically. In other words, the reaction gas mixture input gas will generally be heated first to a temperature of from 500 to 700° C. (or from 550 to 650° C.) (for example by direct firing of the wall surrounding it). Normally, a single adiabatic pass through a catalyst bed will then be sufficient to achieve the desired conversion, in the course of which the reaction gas mixture will cool by from 30° C. to 200° C. (depending on conversion and dilution). The presence of steam as a heat carrier is also noticeably advantageous from the point of view of an adiabatic method. The lower reaction temperature enables longer lifetimes of the catalyst bed used.

In principle, the heterogeneously catalyzed propane dehydrogenation in reaction zone A (irrespectively of whether conducted adiabatically or isothermally) can be carried out either in a fixed bed reactor or else in a moving bed or fluidized bed reactor.

Remarkably, even in adiabatic operation, a single shaft furnace reactor which is flowed through by the reaction gas mixture axially and/or radially can be sufficient as a fixed bed reactor.

In the simplest case, this is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and is substantially heat-insulated in adiabatic operation is flowed through axially by the hot, reaction gas mixture input gas comprising propane. The catalyst geometry may be either spherical or else annular or strand-shaped. Since the reaction volume can be realized in this case by a very inexpensive apparatus, preference is to be given to all catalyst geometries which have a particularly low pressure drop. These are in particular catalyst geometries which lead to a large cavity volume or are structured, for example monoliths or honeycombs. To realize a radial flow of the propane-containing reaction gas mixture, the reactor may, for example, consist of two concentric cylindrical grids disposed in a shell and the catalyst bed may be arranged in their annular gap. In the adiabatic case, the metal shell would in turn be thermally insulated if appropriate.

Useful catalyst charges for a heterogeneously catalyzed propane dehydrogenation with comparatively low propane conversion in single pass are especially the catalysts disclosed in DE-A 199 37 107, in particular all of those disclosed by way of example, and also mixtures thereof with geometric shaped bodies inert with respect to the heterogeneously catalyzed dehydrogenation.

After a prolonged operating time, the aforementioned catalysts can be regenerated in a simple manner, for example, by initially passing air (preferably) diluted with nitrogen and/or steam in first regeneration stages over the catalyst bed at an inlet temperature of from 300 to 600° C., frequently from 400 to 550° C. The catalyst loading with regeneration gas (for example air) may be, for example, from 50 to 10 000 $h^{-1}$ and the oxygen content of the regeneration gas may be from 0.5 to 20% by volume.

In subsequent further regeneration stages, the regeneration gas used under otherwise identical regeneration conditions may be air. Appropriately from an application point of view, it is recommended to flush the catalyst with inert gas (for example $N_2$) before it is regenerated.

Subsequently, it is generally advisable to regenerate with pure molecular hydrogen or with molecular hydrogen diluted with inert gas (preferably steam and/or nitrogen) (the hydrogen content should be $\geq 1\%$ by volume) under otherwise identical conditions.

Figure 1:
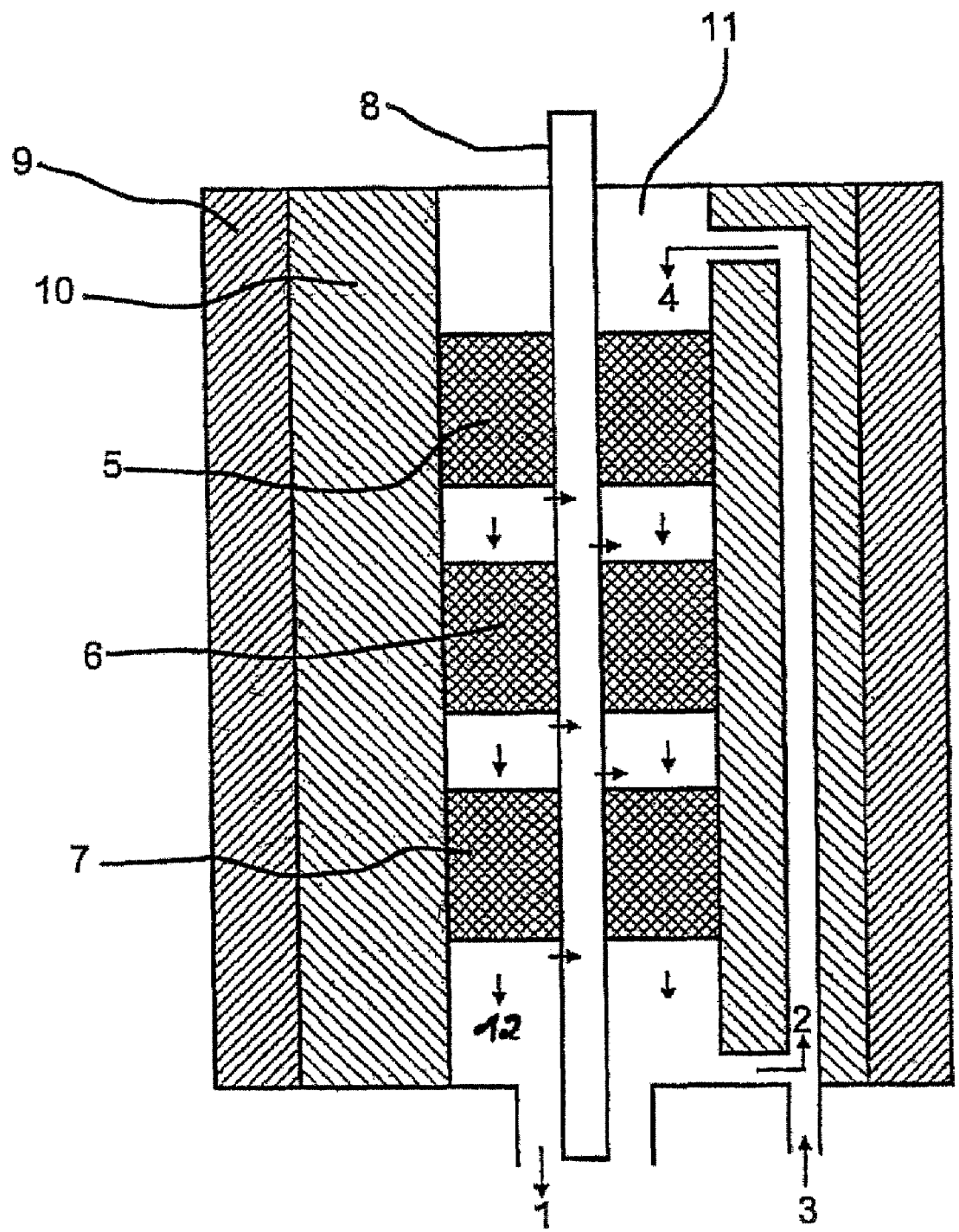
FIG. 1 is a tray loop reactor for the heterogeneously catalyzed propane dehydrogenation to propylene. The reaction is carried out at temperature of 450 to 550° C.

The heterogeneously catalyzed propane dehydrogenation in reaction zone A of the process according to the invention may be carried out with comparatively low propane conversion ($\leq 30$ mol %) in all cases at the same catalyst loadings (based on the total amount of catalyst used) (with regard both to the reaction gas overall and to the propane contained therein) as the variants with high propane conversion (>30 mol %). This loading of reaction gas may be, for example, from 100 to 10 000 $h^{-1}$, frequently from 300 to 5000 $h^{-1}$, i.e. in many cases from about 500 to 3000 $h^{-1}$.

In a particularly elegant manner, the heterogeneously catalyzed propane dehydrogenation (at low propane conversion in particular) in reaction zone A (as already addressed) can be realized in a tray reactor.

This comprises more than one catalyst bed catalyzing the dehydrogenation in spatial succession. The catalyst bed number may be from 1 to 20, appropriately from 2 to 8, or else from 3 to 6. The catalyst beds are preferably arranged in radial or axial succession. From an application point of view, it is appropriate to use the fixed bed catalyst type in such a tray reactor.

In the simplest case, the fixed catalyst beds in a shaft furnace reactor are arranged axially or in the annular gaps of concentric cylindrical grids. However, it is also possible to arrange the annular gaps in segments one above the other and to conduct the gas after it has passed radially through one segment into the next segment above it or below it.

Appropriately, the reaction gas mixture is subjected to intermediate heating in the tray reactor on its path from one catalyst bed to the next catalyst bed, for example by passing it over heat exchanger ribs heated by hot gases or by passing it through pipes heated by hot combustion gases.

When the tray reactor is otherwise operated adiabatically, it is sufficient for propane conversions of $\leq 30$ mol %, in particular when using the catalysts described in DE-A 199 37 107, especially those of the exemplary embodiments, to conduct the reaction gas mixture input gas into the dehydrogenation reactor preheated to a temperature of from 450 to 550° C. (preferably from 450 to 500° C.) and to keep it within this temperature range inside the tray reactor. This means that the entire propane dehydrogenation can thus be realized at very low temperatures, which is found to be particularly favorable for the lifetime of the fixed catalyst beds between two regenerations.

It is even more elegant to carry out the catalytic dehydrogenation in reaction zone A (as likewise already addressed) autothermally, i.e., for example, to carry out the above-outlined intermediate heating by a direct route (autothermal method). To this end, a limited amount of molecular oxygen is added to the reaction gas mixture after it has flowed through the first catalyst bed, between the downstream catalyst beds. Depending on the dehydrogenation catalyst used, limited combustion of the hydrocarbons present in the reaction gas mixture, any coke or coke-like compounds already deposited on the catalyst surface, and/or of hydrogen which has been formed in the course of the heterogeneously catalyzed propane dehydrogenation and/or has been added to the reaction gas mixture can thus be brought about (it may also be appropriate from an application point of view to insert catalyst beds in the tray reactor which are charged with catalyst which particularly specifically (selectively) catalyzes the combustion of hydrogen (and/or of hydrocarbon) (examples of useful catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314); for example, such catalyst beds may be accommodated in the tray reactor in alternation to the beds containing dehydrogenation catalyst). The heat of reaction released thus allows virtually isothermal operation of the heterogeneously catalyzed propane dehydrogenation in a quasi-autothermal manner (quasi-adiabatic reactor configuration). As the selected residence time of the reaction gas in the catalyst bed is increased, propane dehydrogenation is thus possible at decreasing or substantially constant temperature, which enables particularly long lifetimes between two regenerations.

In general, oxygen feeding as described above should be undertaken such that the oxygen content of the reaction gas mixture, based on the amount of propane and propylene present therein, is from 0.01 or 0.5 to 30% by volume. Useful oxygen sources include both pure molecular oxygen and oxygen diluted with inert gas, for example CO, $CO_2$, $N_2$ and/or noble gases, but especially also air. The resulting combustion gases generally have an additional diluting effect and thus promote the heterogeneously catalyzed propane dehydrogenation.

The isothermicity of the heterogeneously catalyzed propane dehydrogenation can be further improved by incorporating closed (for example tubular) internals which have favorably, but not necessarily, been evacuated before filling in the spaces between the catalyst beds in the tray reactor. Such internals may also be placed into the particular catalyst bed. These internals contain suitable solids or liquids which evaporate or melt above a certain temperature, consuming heat as they do so, and, when the temperature falls below this value, condense again and release heat as they do so.

One means of heating the reaction gas mixture input gas for the heterogeneously catalyzed propane dehydrogenation in reaction zone A to the reaction temperature required is to combust a portion of the propane and/or $H_2$ present therein by means of molecular oxygen present in the reaction gas mixture input gas (for example over suitable specific combustion catalysts, for example by simply passing over and/or passing through), and bringing about the heating to the desired (in terms of the dehydrogenation) reaction temperature by means of the heat of combustion thus released. The resulting combustion products, such as $CO_2$, $H_2O$ and the $N_2$ which if appropriate accompanies the molecular oxygen required for the combustion, are advantageously inert diluent gases.

The aforementioned hydrogen combustion can be realized in a particularly elegant manner as described in DE-A 102 11 275, i.e. in a process for continuous heterogeneously catalyzed partial dehydrogenation of propane in reaction zone A, in which a cycle gas 1 comprising molecular oxygen and reaction gas mixture input gas comprising fresh propane and also molecular oxygen and, if appropriate, steam is fed continuously to reaction zone A, the reaction gas mixture input gas is conducted in reaction zone A over at least one fixed catalyst bed and propylene is formed at least partially, if appropriate, further gas comprising molecular oxygen is added to the reaction gas mixture input gas after entry into reaction zone A, the molecular oxygen is oxidized in reaction zone A in the molecular hydrogen present in the reaction gas mixture partly to steam and a product gas mixture A which comprises molecular hydrogen, steam, propylene and propane is withdrawn from reaction zone A, wherein the product gas mixture A withdrawn from reaction zone A is divided into two portions of identical composition and one of the two portions is recycled as cycle gas 2 into the reaction gas mixture input gas for reaction zone A and the other portion used further in accordance with the invention as product gas mixture A.

Advantageously in accordance with the invention, a reaction gas mixture input stream is fed to reaction zone A in the process according to the invention, whose essential contents are typically as follows:

| | |
|---|---|
| propene | from $\geq 0$ to 10, frequently from 0 to 6% by volume; |
| acrolein | from 0 to 1, in many cases from 0 to 0.5, frequently from 0 to 0.25% by volume; |

-continued

| | |
|---|---|
| acrylic acid | from 0 to 0.25, in many cases from 0 to 0.05, frequently from 0 to 0.03% by volume; |
| $CO_x$ | from 0 to 5, in many cases from 0 to 3, frequently from 0 to 2% by volume; |
| propane | from 5 to 50, preferably from 10 to 20% by volume; |
| nitrogen | from 30 to 80, preferably from 50 to 70% by volume; |
| oxygen | from >0 to 5, preferably from 1.0 to 2.0% by volume; |
| $H_2O$ | from $\geqq$0 to 20, preferably from 5.0 to 10.0% by volume; |
| $H_2$ | from 0.5 to 10, preferably from 1 to 5% by volume. |

Acetic acid may also be present in small amounts (about comparable to the possible acrylic acid contents).

While EP-A 117 146, DE-A 22 13 573 and U.S. Pat. No. 3,161,670 recommend using product gas mixture A to charge the at least one oxidation reactor in reaction zone B, it is considered to be advantageous for the process according to the invention to at least partly remove constituents other than propane and propylene present in product gas mixture A therefrom before it is used to obtain the charge gas mixture for the at least one oxidation reactor. This can be done, for example, by passing product gas mixture A, if appropriate after it has been cooled beforehand in an indirect heat exchanger, through a membrane which has generally been configured to a tube and is permeable only to molecular hydrogen. The molecular hydrogen thus obtained can, if required, be recycled partly into reaction zone A (for example as a constituent of the reaction gas mixture input gas) for advantageous configuration of the heterogeneously catalyzed dehydrogenation of propane or sent to another utilization. In addition or alternatively, a portion or the entirety of steam typically present in product gas mixture A may be removed therefrom (for example by condensation) prior to the use of product gas mixture A to charge the oxidation reactor in reaction zone B.

However, advantageously in accordance with the invention, at least 50% by volume, preferably at least 75% by volume, more preferably at least 90% by volume and most preferably at least 95% by volume of the constituents other than propane and propylene present in product gas mixture A will be removed before it is used as the propene source for the partial oxidation in reaction zone B of the process according to the invention. In principle, it is possible for this purpose to employ all removal variants described in the documents DE-A 10 2004 032 129, DE-A 10 2005 013 039, DE-A 10 2005 009 891, DE-A 10 2005 010 111, DE-A 10 2005 009 885, DE-A 10 2005 022 798 and DE-A 10 245 585.

One means appropriate for the inventive requirements consists, for example, in contacting the preferably cooled (preferably to temperatures of from 10 to 100 or 70° C.) product gas mixture A, for example at a pressure of from 0.1 to 50 bar, preferably from 5 to 15 bar, and a temperature of, for example, from 0 to 100° C., preferably from 20 to 40° C., with a (preferably high-boiling) organic solvent (preferably a hydrophobic solvent) in which propane and propylene (appropriately preferentially over the other constituents of product gas mixture A) are absorbed (for example by simply passing it through). Subsequent desorption, rectification and/or stripping with a gas which behaves inertly with regard to the downstream propylene partial oxidation and/or is required as a reactant in this partial oxidation (for example air or another mixture of molecular oxygen and inert gas) can recover the propane and propylene in a mixture in purified form, and this mixture can be used as the propylene source for the partial oxidation (preference is given to proceeding as described in Comparative Example 1 of the German application DE-A 10 2004 032 129). The offgas of such a absorption, which comprises molecular hydrogen if appropriate, can be subjected, for example, to a pressure swing adsorption and/or membrane separation (for example according to DE-A 10235419) and then the removed hydrogen can be used additionally as a constituent of reaction gas mixture input stream A.

However, the C3 hydrocarbons/C4 hydrocarbons separating factor in the above separating process is comparatively limited and frequently insufficient for the requirements described in DE-A 10245585.

As an alternative to the separation step via absorption described, preference is therefore frequently given for the inventive purposes to a pressure swing adsorption or a pressure rectification.

Suitable absorbents for the above-described absorptive removal are in principle all absorbents which are capable of absorbing propane and propylene. The absorbent is preferably an organic solvent which is preferably hydrophobic and/or high-boiling. Advantageously, this solvent has a boiling point (at a standard pressure of 1 atm) of at least 120° C., preferably of at least 180° C., preferentially of from 200 to 350° C., in particular from 250 to 300° C., more preferably from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not contain any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols containing from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyldiphenylmethane and its isomers, 2-methyl-2'-benzyl-diphenylmethane, 2-methyl-4'-benzyldiphenylmethane and 4-methyl-2'-benzyldiphenyl-methane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example from Bayer Aktiengesellschaft). Frequently, this solvent mixture comprises a solvent such as dimethyl phthalate added in an amount of from 0.1 to 25% by weight based on the entire solvent mixture. Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent is $\leqq$300 g/mol. Also suitable are the paraffin oils, described in DE-A 33 13 573, having from 8 to 16 carbon atoms. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type. If they comprise a small residual aromatics content, this may, prior to the use described, advantageously be reduced by rectification and/or adsorption and be lowered to values significantly below 1000 ppm by weight. Further suitable commercial products are n-paraffin ($C_{13}$-$C_{17}$) or Mihagol® 5 Erdöl-Raffinerie-Emsland GmbH, LIN-PAR®14-17 from CONDEA Augusta S.p.A. (Italy) or SASOL Italy S.p.A., normal paraffins (heavy) $C_{14}$-$C_{18}$ from SLOVNAFT in Slovakia.

The contents (reported in area percent of gas chromatography analysis) in the aforementioned products of linear hydrocarbons are typically:

total $C_9$ to $C_{13}$: less than 1%; $C_{14}$: 30 to 40%; $C_{15}$: 20 to 33%; $C_{16}$: 18 to 26%; $C_{17}$: Up to 18%; $C_{\geq 18}$: <2%.

A typical composition of the product from SASOL is: $C_{13}$: 0.48%; $C_{14}$: 39.8%; $C_{15}$: 20.8%; $C_{16}$: 18.9%; $C_{17}$: 17.3%; $C_{18}$: 0.91%; $C_{19}$: 0.21%.

A typical composition of the product from Haltermann is: $C_{13}$: 0.58%; $C_{14}$: 33.4%; $C_{15}$: 32.8%; $C_{16}$: 25.5%; $C_{17}$: 6.8%; $C_{\geq 18}$: <0.2%.

In continuous operation, the composition of the absorbent will change correspondingly as a result of the process.

The performance of the absorption is subject to no particular restrictions. It is possible to use all common processes and conditions known to those skilled in the art. Preference is given to contacting the partial flow 2 of product gas mixture substream 2 with the absorbent at a pressure of from 1 to 50 bar, preferably from 2 to 20 bar, more preferably from 5 to 15 bar, and a temperature of from 0 to 100° C., in particular from 20 to 50 or 40° C. The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000, or to 750 m²/m³, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and the propylene may be removed from the absorbent by stripping, flash evaporation (flashing) and/or distillation.

The propane and propylene are preferably removed from the absorbent by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 30 to 50° C. An example of a gas suitable for the stripping is steam, but preference is given in particular to oxygen/nitrogen mixtures, for example air. When air or oxygen/nitrogen mixtures are used in which the oxygen content is above 10% by volume, it may be sensible to add a gas before and/or during the stripping process which reduces the explosion range. Particularly suitable for this purpose are gases having a specific heat capacity of $\geq 29$ J/mol·K at 20° C., for example methane, ethane, propane (preferred), propene, benzene, methanol, ethanol, and ammonia, carbon dioxide and water. However, preference is given in accordance with the invention to avoiding C4 hydrocarbons as such additives. Particularly suitable for the stripping are also bubble columns with and without internals.

The propane and propylene may also be removed from the absorbent by a distillation or rectification, in which case the columns which are familiar to those skilled in the art and have structured packings, random packings or appropriate internals can be used. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to change the partial oxidation, a propylene source which is suitable in principle for reaction zone B of the process according to the invention and has been obtained from the absorbent by stripping may be fed to a further process stage, in order, for example, to reduce the losses of entrained absorbent (for example separation in demisters and/or depth filters) and to thus simultaneously protect the partial oxidation to be carried out in accordance with the invention from absorbent or in order to further improve the separating action between C3/C4 hydrocarbons. Such a removal of the absorbent may be effected by all process steps known to those skilled in the art. An example of an embodiment of such a removal preferred in the process according to the invention is the quenching of the outlet stream from the stripping apparatus with water. In this case, the absorbent is washed out of this laden outlet stream with water and the outlet stream is simultaneously laden with water (small amounts of water have a promoting effect on the activity of the catalysts for the inventive partial oxidation). This scrubbing or the quenching may be effected, for example, at the top of a desorption column using a liquid collecting tray by counterspraying of water or in a dedicated apparatus.

To support the separating effect, it is possible to install internals which increase the quench surface area in the quench chamber, as are known to those skilled in the art from rectifications, absorptions and desorptions.

Water is a preferred scrubbing agent in that it normally does not interfere in the downstream partial oxidation. After the water has washed the absorbent out of the outlet stream laden with propane and propylene, the water/absorbent mixture may be fed to a phase separation and the treated, low-volume outlet stream fed directly to partial oxidation to be carried out in accordance with the invention.

In a manner advantageous for the process according to the invention, especially when the propylene/propane mixture is stripped by means of air to free it of the absorbate, starting reaction gas mixtures usable for the partial oxidation can generally be obtained directly. In the case that their propane content should not yet be satisfactory in accordance with the invention, it is possible also to add fresh propane to them before they are used for the partial oxidation of the propylene present to be carried out in accordance with the invention. Via the residual gas (cycle gas 1), fresh propane is then appropriately recycled into the heterogeneously catalyzed dehydrogenation (as a constituent of the reaction gas mixture input stream conducted into reaction zone A). The direct supply of fresh propane into reaction zone A can then be reduced by the appropriate amount of propane. In the extreme case, the supply of fresh propane required for the heterogeneously catalyzed propane dehydrogenation immediately into reaction zone A in the process according to the invention can be dispensed with entirely when this fresh propane, before the partial oxidation of propylene is carried out, is supplied fully into this starting reaction gas mixture, whence it is then fed as a remaining constituent in the residual gas (cycle gas 1) only after passing through the partial oxidation to be carried out in accordance with the invention, to reaction gas mixture input stream for the heterogeneously catalyzed propane dehydrogenation of reaction zone A. If appropriate, fresh propane may also be supplied in the process according to the invention into any $C_3$ removal (for example as stripping gas) disposed between heterogeneously catalyzed dehydrogenation and propylene partial oxidation.

When the reaction is a two-stage partial oxidation of propylene to acrylic acid, some or even all of the fresh propane may also be supplied into the starting reaction gas mixture for the second stage of the partial oxidation (however, this starting reaction gas mixture is sometimes not explosive even when this qualification was actually true for the starting reaction gas mixture for the first stage of the partial oxidation). This is advantageous in particular because the undesired side reaction of propane to give propionaldehyde and/or propionic acid starts in particular from the first partial oxidation stage (propylene→acrolein) under the conditions thereof. It is also advantageous to divide a fresh propane supply substantially uniformly between the first and the second partial oxidation stage.

As a result of this possibility of supplying fresh propane into the starting reaction gas mixture for the partial oxidation stages, the composition of these starting reaction gas mixtures can reliably be made nonexplosive. If appropriate, a portion of residual gas can also be recycled directly into the propylene and/or acrolein partial oxidation for this purpose. If required, it is also possible to use a mixture of fresh propane and residual gas for this purpose. A crucial factor in answering the question of whether the starting reaction gas mixture for a partial oxidation stage is explosive or not is whether combustion (ignition, explosion) initiated by a local ignition source (for example glowing platinum wire) spreads in the starting reaction gas mixture under certain starting conditions (pressure, temperature) or not (cf. DIN 51649 and the experiment description in WO 04/007405). When there is spreading, the mixture shall be referred to here as explosive. When there is no spreading, the mixture is classified as nonexplosive in this document. When the starting reaction gas mixture is nonexplosive, this also applies to the reaction gas mixtures formed in the course of the inventive partial oxidation of propylene (cf. WO 04/007405).

In general, however, only the reaction gas mixture input gas stream fed to reaction zone A will comprise added fresh propane in the process according to the invention.

The present invention also relates to process configurations in which the fresh propane required for the process is supplied at most partly (for example only to an extent of 75%, or only to extent of 50%, or only to an extent of 25%) to reaction gas mixture input stream A and at least partly (generally the remainder, if appropriate the entirety) to the reaction gas mixture starting gas(es) of the partial oxidation. Otherwise, the procedure may be as described in WO 01/96170, which forms an integral part of this application.

In a manner known per se, the heterogeneously catalyzed gas phase partial oxidation of propylene to acrylic acid with molecular oxygen proceeds in principle in two steps successive along the reaction coordinate, of which the first leads to acrolein, and the second from acrolein to acrylic acid.

This reaction sequence in two steps successive in time opens up the possibility in a manner known per se of terminating the process according to the invention at the stage of acrolein (the stage of predominant acrolein formation) and undertaking the target product removal at this stage, or continuing the process according to the invention up to predominant acrylic acid formation and only then undertaking the target product removal.

When the process according to the invention is carried out up to predominant acrylic acid formation, it is advantageous in accordance with the invention to perform the process in two stages, i.e. in two oxidation stages arranged in series, in which case the fixed catalyst bed to be used and preferably also the other reaction conditions, for example the temperature of the fixed catalyst bed, are appropriately adjusted in an optimizing manner in each of the two oxidation stages.

Although the multimetal oxides comprising the elements Mo, Fe, Bi which are particularly suitable as active compositions for the catalysts of the first oxidation stage (propylene→acrolein) are also capable to a certain extent of catalyzing the second oxidation stage (acrolein→acrylic acid), preference is normally given for the second oxidation stage to catalysts whose active composition is at least one multimetal oxide comprising the elements Mo and V.

The process according to the invention for the heterogeneously catalyzed partial oxidation of propylene over fixed catalyst beds whose catalysts have, as an active composition, at least one multimetal oxide comprising the elements Mo, Fe and Bi is thus suitable in particular as a one-stage process for preparing acrolein (and acrylic acid if appropriate) or as the first reaction stage for the two-stage preparation of acrylic acid.

The realization of the one-stage heterogeneously catalyzed partial oxidation of propylene to acrolein and acrylic acid if appropriate or the two-stage heterogeneously catalyzed partial oxidation of propylene to acrylic acid using an inventive starting reaction gas mixture may specifically be carried out as described in the documents EP-A 700 714 (first reaction stage; as described there, but also in corresponding countercurrent mode of salt bath and starting reaction gas mixture over the tube bundle reactor), EP-A 70 08 93 (second reaction stage; as described there, but also in corresponding countercurrent mode), WO 04/085 369 (especially this document is considered to be an integral part of this document) (as a two-stage process), WO 04/85363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (one-stage or two-stage), WO 04/085368 (as a two-stage process), DE 10 2004 021 764 (two-stage), WO 04/085362 (first reaction stage), WO 04/085370 (second reaction stage), WO 04/085365 (second reaction stage), WO 04/085367 (two-stage), EP-A 990 636, EP-A 1 007 007 and EP-A 1 106 598.

This is especially true of all working examples contained in these documents. They may be carried out as described in these documents, but with the difference that the starting reaction gas mixture used for the first reaction stage (propylene to acrolein) is a starting reaction gas mixture obtained according to the present invention. Regarding the remaining parameters, the procedure is as in the working examples of the documents mentioned (especially regarding the fixed catalyst beds and reactant loading on the fixed catalyst beds). When the procedure in the aforementioned working examples of the prior art is in two stages and there is secondary oxygen (secondary air) feeding between the two reaction stages, the feeding is undertaken in an appropriate manner, but is adjusted in its amount to the effect that the molar ratio of molecular oxygen to acrolein in the charge mixture of the second reaction stage corresponds to that in the working examples of the documents mentioned. An inventive starting reaction gas mixture for the heterogeneously catalyzed partial gas phase oxidation is obtainable in a simple manner, for example, by adding as much molecular oxygen to product gas mixture A or to product gas mixture stream A' as is required for the partial oxidation. This supply can be effected in the form of pure molecular oxygen or else in the form of a mixture of molecular oxygen and of inert gas (or else only in the presence of inert gas). Preference is given in accordance with the invention to air as such a mixture. It is essential to the invention that this oxygen supply is effected in such a way that product gas mixture B still comprises unconverted molecular oxygen.

In general, the molar ratio of molecular oxygen present in the starting reaction gas mixture for the partial oxidation to propylene present in the starting reaction gas mixture for the partial oxidation is $\geq 1$ and $\geq 3$.

Multimetal oxide catalysts particularly suitable for the particular reaction stage have been described many times before and are well known to those skilled in the art. For example, EP-A 253 409 refers on page 5 to corresponding US patents.

Favorable catalysts for the particular oxidation stage are also disclosed by DE-A 4 431 957, DE-A 10 2004 025 445 and DE-A 4 431 949. This is especially true of those of the general formula I in the two aforementioned documents. Particularly advantageous catalysts for the particular oxidation stage are disclosed by the documents DE-A 103 25 488, DE-A 103 25 487, DE-A 103 53 954, DE-A 103 44 149, DE-A 103 51 269, DE-A 103 50 812, DE-A 103 50 822.

For the inventive reaction stage for the heterogeneously catalyzed gas phase partial oxidation of propylene to acrolein or acrylic acid or a mixture thereof, useful multimetal oxide compositions are in principle all multimetal oxide compositions comprising Mo, Bi and Fe as the active composition.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 700 714.

Also suitable for this reaction stage are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 279 374, DE-A 330 00 44, EP-A 575 897, US-A 4 438 217, DE-A 19855913, WO 98/24746, DE-A 197 46 210 (those of the general formula II), JP-A 91/294 239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to Example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to Example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein and, if appropriate, acrylic acid can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e =from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form.

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the "propylene→acrolein (and acrylic acid if appropriate)" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions to be used for the step from propylene to acrolein (and if appropriate acrylic acid) are also compositions of the general formula V

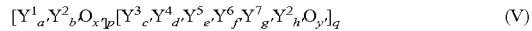

$$[Y^1_a, Y^2_b, O_{x'}]_p[Y^3_{c'}, Y^4_{d'}, Y^5_{e'}, Y^6_{f'}, Y^7_{g'}, Y^2_{h'}, O_{y'}]_q \quad (V)$$

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and
p,q=numbers whose p/q ratio is from 0.1 to 10, comprising three-dimensional regions of the chemical composition $Y^1_a, Y^2_b, O_{x'}$, which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions V in accordance with the invention are those in which $Y^1$ is only bismuth.

Among these, preference is given in turn to those of the general formula VI

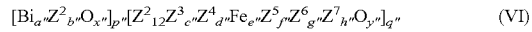

$$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \quad (VI)$$

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h''from 0 to 1, x″,y″=numbers which are determined by the valency and frequency of the elements in VI other than oxygen,
p″,q″=numbers whose p″/q″ ratio is from 0.1 to 5, preferably from 0.5 to 2, and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_a Y^2_b O_x]_p$ ($[Bi_a Z^2_b O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_a Y^2_b O_{x'} [Bi_{a''} Z^2_{b''} O_{x''}]$ which are delimited from their local environment owing to their different chemical composition from their local environment, and whose maximum diameter is in the range from 1 nm to 100 µm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the second step (the second reaction stage), the heterogeneously catalyzed gas phase partial oxidation of acrolein to acrylic acid, useful active compositions for the catalysts required are, as already stated, in principle all multimetal oxide compositions comprising Mo and V, for example those of DE-A 100 46 928.

A multitude thereof, for example those of DE-A 198 15 281, can be encompassed by the general formula VII

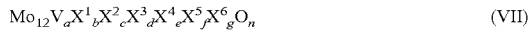

$$Mo_{12}V_a X^1_b X^2_c X^3_d X^4_e X^5_f X^6_g O_n \qquad (VII)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly preferred in accordance with the invention are those of the general formula VIII

$$Mo_{12}V_{a'} Y^1_{b'} Y^2_{c'} Y^5_{f'} Y^6_{g'} O_{n'} \qquad (VIII)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length× internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step are also compositions of the general formula IX

   (IX)

in which the variables are each defined as follows:
D=$Mo_{12}V_{a''}Z^1_{b''}Z^2_{c''}Z_{3d''}Z^4_{e''}Z^5_{f''}Z^6_{g''}O_{x'''}$,
E=$Z^7_{12}CU_{h''}H_{i''}O_{y'''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x''y''=numbers which are determined by the valency and frequency of the elements in IX other than oxygen and
p,q=numbers other than zero whose p/q ratio is from 160:1 to 1:1, and which are obtainable by separately preforming a multimetal oxide composition E

   (E)

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D

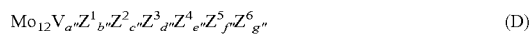   (D)

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein acrylic acid" step are also those of DE-A 198 15281, especially having multimetal oxide active compositions of the general formula I of this document.

Advantageously, unsupported catalyst rings are used for the step from propylene to acrolein and coated catalyst rings for the step from acrolein to acrylic acid.

The performance of the partial oxidation of the process according to the invention, from propylene to acrolein (and acrylic acid if appropriate), may be carried out with the catalysts described, for example, in a single-zone multiple catalyst tube fixed bed reactor, as described by DE-A 4 431 957. In this case, reaction gas mixture and heat carrier (heat exchange medium) may be conducted in cocurrent or in countercurrent viewed over the reactor.

The reaction pressure is typically in the range from 1 to 3 bar and the overall space velocity on the fixed catalyst bed of (starting) reaction gas mixture 2 is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or ≧140 l (STP)/l·h, or ≧150 l (STP)/l·h, or ≧160 l (STP)/l·h are particularly preferred in accordance with the invention, since the inventive starting reaction gas mixture, owing to the presence of unconverted propane, causes favorable hotspot behavior (all of the aforementioned applies irrespective of the specific selection of the fixed bed reactor).

The flow to the single-zone multiple catalyst tube fixed bed reactor of the charge gas mixture is preferably from above. The heat exchange medium used is appropriately a salt melt, preferably consisting of 60% by weight of potassium nitrate (KNO$_3$) and 40% by weight of sodium nitrite (NaNO$_2$), or of 53% by weight of potassium nitrate (KNO$_3$), 40% by weight of sodium nitrite (NaNO$_2$) and 7% by weight of sodium nitrate (NaNO$_3$).

Viewed over the reactor, salt melt and reaction gas mixture may, as already stated, be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 30 or up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Research Disclosure No. 497012 of Aug. 29, 2005, or according to Example 1 of DE-A 100 46 957 or according to Example 3 of DE-A 100 46 957 and the inert material used is steatite rings having the geometry 7 mm×7 mm×4 mm (external diameter× height×internal diameter). With regard to the salt bath temperature, the statements of DE-A 4 431 957 apply.

However, the performance of the inventive partial oxidation, from propylene to acrolein (and acrylic acid if appropriate), may also be carried out with the catalysts described, for example, in a two-zone multiple catalyst tube fixed bed reactor, as described by DE-A 199 10 506, DE-A 10 2005 009 885, DE-A 10 2004 032 129, DE-A 10 2005 013 039 and DE-A 10 2005 009 891, and also DE-A 10 2005 010 111. In both of the above-described cases (and quite generally in the process according to the invention), the propene conversion achieved in single pass is normally at values of ≧90 mol %, or ≧95 mol %, and the selectivity of acrolein formation at values of ≧90 mol %. Advantageously in accordance with the invention, the inventive partial oxidation of propene to acrolein, or acrylic acid or mixtures thereof, is effected as described in EP-A 1 159 244 and most preferably as described in WO 04/085 363 and in WO 04/085 362.

The documents EP-A 1 159 244, WO 04/085 363 and WO 04/085 362 are considered to be an integral part of this document.

In other words, the inventive partial oxidation of propylene can be carried out particularly advantageously over a fixed catalyst bed having increased propylene loading and at least two temperature zones.

In this regard, reference is made, for example, to EP-A 1 159 244 and WO 04/085 362. A typical composition of the starting reaction gas mixture for the partial oxidation of propylene to acrolein may, in the process according to the invention, comprise:

from 5 to 9% by volume of propylene,
from 8 to 18% by volume of molecular oxygen,
from 6 to 30 (or to 35)% by volume of propane and
from 32 to 72% by volume of molecular nitrogen.

The performance of the second step in the case of a two-stage partial oxidation of propylene to acrolein, i.e. the partial oxidation of acrolein to acrylic acid, may be carried out with the catalysts described, for example, in a one-zone multiple catalyst tube fixed bed reactor as described in DE-A 44 31 949. In this reaction stage, reaction gas mixture and heat carrier can be conducted in cocurrent viewed over the reactor. In general, the product gas mixture of the preceding inventive propylene partial oxidation to acrolein is in principle conducted as such (if appropriate after intermediate cooling (this may be effected indirectly or directly by, for example, secondary air addition) thereof), i.e. without secondary component removal, into the second reaction stage, i.e. into the acrolein partial oxidation.

The molecular oxygen required for the second step, the acrolein partial oxidation, may already be present in the starting reaction gas mixture for the inventive propylene partial oxidation to acrolein. However, it may also be added partly or fully directly to the product gas mixture of the first reaction stage, i.e. the inventive propylene partial oxidation to acrolein (this is preferably effected in the form of (secondary) air, but may also be effected in the form of pure oxygen or of mixtures of inert gas or oxygen). Irrespective of the procedure, the charge gas mixture (starting reaction gas mixture) of such a partial oxidation of acrolein to acrylic acid advantageously has the following contents:

| | |
|---|---|
| from 4 to 8% by volume of | acrolein, |
| from 2.25 or 4.5 to 9% by volume of | molecular oxygen, |
| from 6 to 30% by volume of | propane, |
| from 32 to 72% by volume of | molecular nitrogen, and |
| from 5 to 15% by volume of | steam. |

The aforementioned starting reaction gas mixture preferably has the following contents:

| | |
|---|---|
| from 5 to 8% by volume of | acrolein, |
| from 2.75 or 5.5 to 9% by volume of | molecular oxygen, |
| from 10 to 25% (or 30%) by volume of | propane, |
| from 40 to 70% by volume of | molecular nitrogen, and |
| from 5 to 15% by volume of | steam. |

The aforementioned starting reaction gas mixture most preferably has the following contents:

| | |
|---|---|
| from 5 to 8% by volume of | acrolein (preferably from 6 to 7% by volume) |
| from 3 or 6 to 9% by volume of | molecular oxygen, |
| from 10 to 20% (or 30%) | propane (preferably from 10 |

| | |
|---|---|
| by volume of from 50 to 65% by volume of from 7 to 13% by volume of | to 16% by volume) molecular nitrogen, and steam, | the preferred ranges applying independently of one another, but advantageously being realized simultaneously.

As in the first reaction stage (propylene→acrolein), the reaction pressure in the second reaction stage (acrolein→acrylic acid) too is typically in the range from 1 to 3 bar and the total space velocity on the fixed catalyst bed of (starting) reaction gas mixture is preferably from 1500 to 4000 or 6000 l (STP)/l·h or more. The acrolein loading (the acrolein hourly space velocity on the fixed catalyst bed) is typically from 90 to 190 l (STP)/l·h, or to 290 l (STP)/l·h or more. Acrolein loadings above 135 l (STP)/l·h, or $\geq 140$ l (STP)/l·h, or $\geq 150$ l (STP)/l·h, or $\geq 160$ l (STP)/l·h are particularly preferred, since the starting reaction gas mixture to be used in accordance with the invention likewise causes favorable hotspot behavior owing to the presence of propane.

The acrolein conversion based on single pass of the reaction gas mixture through the fixed catalyst bed is appropriately normally $\geq 90$ mol % and the accompanying selectivity of acrylic acid formation $\geq 90$ mol %.

The flow to the single-zone multiple catalyst tube fixed bed reactor of the charge gas mixture is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 30 (or up to 20)% by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 30 (or 20)% by weight of inert material and subsequently with from >20% by weight to 50 or to 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to preparation example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion achieved in single pass is normally $\geq 90$ mol %, or $\geq 95$ mol % or $\geq 99$ mol %.

However, the performance of the partial oxidation of acrolein to acrylic acid may also be carried out with the catalysts described, for example, in a two-zone multiple catalyst tube fixed bed reactor as described in DE-A 199 10 508. For the acrolein conversion, the above statements apply. Also in the case in which an acrolein partial oxidation as described above is carried out as the second reaction stage of a two-stage propylene oxidation to acrylic acid in a two-zone multiple catalyst tube fixed bed reactor, the charge gas mixture (starting reaction gas mixture) will appropriately be obtained directly by using the product gas mixture of the partial oxidation directed to the first step (if appropriate after indirect or direct (for example by supplying secondary air) intermediate cooling thereof) (as has already been described above). The oxygen required for the acrolein partial oxidation is preferably added in the form of air (if appropriate also in the form of pure molecular oxygen or in the form of a mixture of molecular oxygen and an inert gas) and, for example, added directly to the product gas mixture of the first step of the two-stage partial oxidation (propylene→acrolein). However, it may also, as already described, already be present in the starting reaction gas mixture for the first reaction stage.

In a two-stage partial oxidation of propylene to acrylic acid with direct further use of the product gas mixture of the first step of the partial oxidation to charge the second step of the partial oxidation, two one-zone multiple catalyst tube fixed bed reactors (at high reactant loading on the catalyst bed, as is quite generally the case, preference is given to cocurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Between the reactors may be disposed an intermediate cooler (for example a tube bundle heat exchanger through whose tubes (which preferably comprise (preferably stainless steel) spirals inserted centrally to increase the heat transfer) the reaction gas is conducted) which may if appropriate comprise inert beds which can perform a filter function. The salt bath temperature of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input and their output temperature is generally $\leq 5°$ C. As already mentioned, both steps of the partial oxidation of propylene to acrylic acid may also be implemented in one reactor over one charge, as described in DE-A 101 21 592.

It should also be mentioned once again that a portion of the starting reaction gas mixture for the first step ("propylene→acrolein") may be residual gas coming from the partial oxidation.

This is, as already stated, a gas which comprises molecular oxygen and remains after the target product removal (acrolein and/or acrylic acid removal) from the product gas mixture of the partial oxidation and may be recycled partly as inert diluent gas into the charge for the first and/or if appropriate second step of the partial oxidation of propylene to acrolein and/or acrylic acid.

ever, such residual gas comprising propane, molecular oxygen and any unconverted propylene will preferably, advantageously in accordance with the invention, be recycled exclusively as cycle gas 1 into the heterogeneously catalyzed propane dehydrogenation in reaction zone A.

Overall, a tube bundle reactor within which the catalyst charge changes appropriately along the individual catalyst tubes with completion of the first reaction step (such two-stage propylene partial oxidations in a single reactor are taught, for example, by EP-A 911 313, EP-A 979 813, EP-A 990 636 and DE-A 28 30 765) forms the simplest implementation form of two oxidation stages for the two steps of the partial oxidation from propylene to acrylic acid. If appropriate, the charge of the catalyst tubes with catalyst is interrupted by an inert material bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert material bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture which leaves the first oxidation zone. The reaction temperature in the first reaction stage (propylene→acrolein) is generally from 300 to 450° C., preferably from 320 to 390° C. The reaction temperature in the second reaction stage (acrolein→acrylic acid) is generally from 200 to 370° C., frequently from 220 to 330° C. The reaction pressure in both oxidation zones is appropriately from 0.5 to 5 bar, advantageously from 1 to 3 bar. The loading (I (STP)/I·h) on the oxidation catalysts of reaction gas in both reaction stages is frequently from 1500 to 2500 I (STP)/I·h or to 4000 I (STP)/I·h. The loading of propylene may be from 100 to 200 or 300 and more I (STP)/I·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry has an advantageous effect on the kinetics of the particular gas phase partial oxidation and on the catalyst lifetime. In the second reaction stage, it is obligatory in accordance with the invention.

In principle, it is also possible to realize the heterogeneously catalyzed gas phase partial oxidation of propylene to acrylic acid to be carried out in accordance with the invention in a single one-zone tube bundle reactor as follows. Both reaction steps proceed in an oxidation reactor which is charged with one or more catalysts whose active composition is a multimetal oxide which comprises the elements Mo, Fe and Bi and is capable of catalyzing the reaction of both reaction steps. This catalyst charge can of course change continuously or abruptly along the reaction coordinate. Of course, it is possible in one embodiment of an inventive two-stage partial oxidation of propylene to acrylic acid in the form of two oxidation stages connected in series to partly or fully remove carbon dioxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons.

In the process according to the invention, metering of, for example, cold air to the product gas mixture of the first partial oxidation stage can also bring about cooling thereof by a direct route before it is used further as a constituent of a starting reaction gas mixture for the second partial oxidation stage.

Advantageously in accordance with the invention, the partial oxidation of acrolein to acrylic acid is effected as described in EP-A 1 159 246 and most preferably as described in WO 04/085 365 and in WO 04/085 370. However, preference is given in accordance with the invention to using, as the starting reaction gas mixture comprising acrolein, a starting reaction gas mixture which is the product gas mixture of an inventive first-stage partial oxidation of propylene to acrolein, which has if appropriate been supplemented with sufficient secondary air that the ratio of molecular oxygen to acrolein in the resulting starting reaction gas mixture is in each case from 0.5 to 1.5. The documents EP-A 1 159 246, WO 04/08 536 and WO 04/085 370 are considered to be an integral part of this document.

In other words, the inventive partial oxidation of acrolein to acrylic acid can be carried out with increased acrolein loading advantageously over a fixed catalyst bed which has at least two temperature zones.

Overall, a two-stage partial oxidation of propylene to acrylic acid will preferably be carried out as described in EP-A 1 159 248 or in WO 04/085 367 or WO 04/085 369.

The product gas mixture stream B which leaves the partial oxidation to be carried out in accordance with the invention (after the first and/or the second reaction stage) is, in the case of a preparation of acrolein and/or acrylic acid, composed substantially of the target product acrolein or acrylic acid or a mixture thereof with acrolein, unconverted molecular oxygen (with a view to the lifetime of the catalysts used, it is favorable in many cases when the oxygen content in the product gas mixture of both partial oxidation stages is still, for example, from at least 1.5 to 4% by volume), propane, unconverted propylene, molecular nitrogen, steam which has formed as a by-product and/or has been used as a diluent gas, carbon oxides which have been formed as a by-product and/or used as a diluent gas, and small amounts of other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid), in some cases further hydrocarbons, for example C4 hydrocarbons (e.g. butene-1 and possible other butenes), and other inert diluent gases.

Useful processes for removing target product present in product gas mixture stream B for the process according to the invention are in principle all processes known in this regard in the prior art. They essentially feature the conversion of the target product from the gaseous into the condensed phase, for example by absorptive and/or condensative methods. Useful absorbents are, for example, water, aqueous solution and/or organic solvents. In the context of this "condensation" of the target product, a residual gas which is not transferred to the condensed phase normally remains, which comprises the constituents of the product gas mixture stream B which are comparatively difficult to condense. These are typically in particular those components whose boiling point at standard pressure (1 bar) is $\leq -30°$ C. (their total proportion in the residual gas is generally $\geq 70\%$ by volume, frequently $\geq 80\%$ by volume and in many cases $\geq 90\%$ by volume). These include primarily unconverted propane, excess molecular oxygen remaining in product gas mixture stream B and any unconverted propylene. In addition, the residual gas will generally comprise inert diluent gases, for example $N_2$, $CO_2$, noble gases (He, Ne, Ar, etc.), CO, and also, to a minor extent, acrylic acid, acrolein and/or $H_2O$ (the steam content in the residual gas may be up to 25% by volume, frequently up to 20% by volume, or up to 10% by volume, but in many cases also below 10% by volume or below 5% by volume) and any secondary components such as ethane, methane and ethylene. This aforementioned residual gas (based on the amount of propane present therein) normally forms the majority (typically at least 80%, or at least 90%, or at least 95% or more) of the residual gas formed in separation zone B and is therefore referred to in this document, inter alia, also as main residual gas.

According to the invention, at least a portion of this residual gas which comprises unconverted propane, molecular oxygen and any unconverted propylene (main residual gas), in cycle gas mode, is recycled into reaction zone A as the gaseous cycle gas 1. Appropriately in accordance with the invention, the entirety of this residual gas is recycled repeatedly as the cycle gas 1 into reaction zone A.

Especially when the condensation of the target product is effected by absorption by means of an organic solvent, at least one second residual gas comprising unconverted propane and any unconverted propylene is generally obtained in separation zone B (based on propane present therein, its amount is normally substantially smaller in comparison to the amount of main residual gas). This is attributable to the condensed phase which forms also taking up unconverted propane and any unconverted propylene to a certain extent.

In the further course of the extractive, distillative, crystallizative and/or desorptive removal of the target product from the condensed phase, this unconverted propane and any propylene is normally recovered as a constituent of at least one further gas phase and, in the process according to the invention, preferably likewise recycled into reaction zone A.

This can be done, for example, in a mixture with the main residual gas (in that case, referred to in this document as overall residual gas). However, it can also be done in the form of gas streams to be recycled independently into reaction zone A. These gas streams to be recycled independently may be free of oxygen or else comprise oxygen (secondary residual gas) (for example when it is obtained by stripping by means of air or at the top of a rectification column flushed by means of air as a polymerization inhibitor).

In the context of this invention, main residual gas, overall residual gas and secondary residual gas form residual gas which comprises unconverted propane, molecular oxygen and any unconverted propylene and can be recycled into reaction zone A as cycle gas 1. According to the invention, molecular oxygen-free residual gas which is obtained in separation zone B and comprises unconverted propane and any unconverted propylene can be recycled into reaction zone A in a mixture with main residual gas and/or secondary residual gas (i.e., for example, as a constituent of overall residual gas), for example as a constituent of cycle gas 1 and/or independently (in this case, the residual gas is not residual gas recycled in reaction zone A in the context of the invention). In the latter case, this recycling can be effected without any restriction, i.e., for example, even as a further gaseous stream, for example cycle gas 3 stream. Especially when substantially all constituents other than propane and propylene present in the product gas mixture are removed therefrom in a first separation zone A in the process according to the invention and the resulting product gas mixture A' is used to charge the at least one oxidation reactor, substantially the entirety of the gas streams which comprise unconverted propane and any unconverted propylene and are obtained in separation zone B will, in the process according to the invention, be recycled into reaction zone A, preferably as a constituent of overall residual gas as cycle gas 1. However, it would also be possible if appropriate to use portions (as described, for example in DE-A 10 2004 032 129) for other purposes, for example for energy generation and/or synthesis gas preparation and/or as a diluent gas in reaction zone B. In general, in the above-described case, however, at least half or two thirds (i.e. 50% by volume or 66.6% by volume), preferably at least three quarters and most preferably the entirety of the aforementioned residual gas obtained in separation zone B (in each case individually with regard to the main and/or secondary or overall residual gas) will be recycled into reaction zone A. When only one residual gas stream comprising unconverted propane, molecular oxygen and unconverted propylene is obtained in separation zone B (this is frequently the general case), it is, especially when substantially all constituents other than propane and propylene present in the product gas mixture are removed therefrom in a first separation zone A in the process according to the invention and the resulting product gas mixture A' is used to charge at least one oxidation reactor, recycled preferably fully in accordance with the invention (if appropriate minus a portion of identical composition conducted as diluent gas into reaction zone B) into reaction zone A as cycle gas 1. It can then also be divided into two portions of identical composition and, as described above, only one portion is recycled into reaction zone A as cycle gas 1 and the other portion used further in another way. When more than one such residual gas stream is obtained in separation zone B, these residual gas streams (as already mentioned) may, in accordance with the invention, be recycled together (for example combined) in reaction zone A as cycle gas 1. It will be appreciated that the recycling of these residual gas streams into reaction zone A can also be effected individually. It is also possible for a portion or the entirety of cycle gas 1 to be recycled into reaction zone A not into the reaction gas input mixture fed to reaction zone A but rather not until along the reaction path of the heterogeneously catalyzed dehydrogenation of propane in reaction zone A. The reaction path of the heterogeneously catalyzed dehydrogenation of propane in the first reaction zone A shall be understood to mean the flow path of the propane present in the reaction gas mixture input stream through reaction zone A as a function of the dehydrogenating conversion (the conversion in the heterogeneously catalyzed dehydrogenation) of this propane.

Residual gas recycled into reaction zone A as cycle gas 1 in the process according to the invention normally consists to an extent of $\geq 70\%$ by volume, frequently to an extent of $\geq 80\%$ by volume and in many cases to an extent of $\geq 90\%$ by volume, usually to an extent of $\geq 95\%$ by volume or to an extent of $\geq 98\%$ by volume of constituents whose boiling point at standard pressure (1 bar) is $\leq -30°$ C.

Especially when substantially all constituents other than propane and propylene present in product gas mixture A are removed therefrom in a first separation zone A in the process according to the invention and the resulting product gas mixture A' is used to charge at least one oxidation reactor, the composition of the cycle gas 1 comprises typically:

from 0 to 2% by volume, in many cases from 0 to 1% by volume, frequently
from 0 to 0.5% by volume of propene;
from 0 to 2% by volume, in many cases from 0 to 1% by volume, frequently
from 0 to 0.5% by volume of acrolein;
from 0 to 0.5% by volume, in many cases from 0 to 0.1% by volume, frequently
from 0 to 0.05% by volume of acrylic acid;
from 0 to 4% by volume, in many cases from 0 to 2% by volume, frequently
from 0 to 1.5% by volume of $CO_x$;
from 10 to 50% by volume, in many cases from 20 to 30% by volume of propane;
from 0 to 70% by volume, in many cases from 40 to 70% by volume of $N_2$;
from 1 to 10% by volume, in many cases from 2 to 5% by volume, frequently
from 2.5 to 3.5% by volume of $O_2$ and
from >0 to 15% by volume of $H_2O$.

In addition, small amounts of secondary components such as ethane, methane and ethylene may be present. Frequently, cycle gas 1 in the process according to the invention has a temperature of from 50 to 200° C., or from 70 to 130° C., and a pressure of from 1.5 to 5 bar, preferably from 3 to 4 bar.

In accordance with the above, the target product may be removed from product gas mixture B in a manner known per se in a second separation zone B (for example by partial or full and, if appropriate, fractional condensation of acrylic acid, or by absorption of acrylic acid in water or in a high-boiling hydrophobic organic solvent, or by absorption of acrolein in water or in aqueous solutions of lower carboxylic acids and subsequent workup of the condensates and/or absorbates; according to the invention, product gas mixture B will preferably be fractionally condensed; cf., for example, EP-A 1 388 533, EP-A 1 388 532, DE-A 102 35 847, EP-A 792 867, WO 98/01 415, EP-A 1 015 411, EP-A 1 015 410, WO 99/50 219, WO 00/53 560, WO 02/09 839, DE-A 102 35 847, WO 03/041 833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 1 041 062, EP-A 117 146, DE-A 43 08 087, DE-A 43 35 172, DE-A 44 36 243, DE-A 199 24 532, DE-A 103 32 758 and DE-A 199 24 533). An acrylic acid removal may also be undertaken as in EP-A 982 287, EP-A 982 289, DE-A 103 36 386, DE-A 101 15 277, DE-A 196 06 877, DE-A 197 40 252, DE-A 196 27 847, EP-A 920 408, EP-A 1 068 174, EP-A 1 066 239, EP-A 1 066 240, WO 00/53 560, WO 00/53 561, DE-A 100 53 086 and EP-A 982 288. Preference is given to removing as described in FIG. 7 of WO/0 196 271 or as described in DE-A 10 2004 032 129 and its equivalent patents. Favorable removal methods are also the processes described in the documents WO 04/063 138, WO 04/35 514, DE-A 102 43 625 and DE-A 102 35 847. Crude acrylic acid obtained in this way may be further processed, for example, as described in the documents WO 01/77 056, WO 03/041 832, WO 02/055 469, WO 03/078 378 and WO 03/041 833.

A common feature of the above separating processes is (as already mentioned) that a residual gas stream which comprises substantially those constituents of product gas mixture B whose boiling point at standard pressure (1 bar) is ≦−30° C. (i.e. the constituents which are difficult to condense or else volatile) normally remains at the top of the particular separating column which comprises separating internals and in whose lower section product gas mixture B is fed, normally after preceding direct and/or indirect cooling thereof. This includes especially excess molecular oxygen remaining in product gas mixture B.

In the lower section of the separating column, the less volatile constituents of product gas mixture B, including the particular target product, are normally obtained in the condensed phase.

The residual gas constituents are primarily propane, any propylene which has not been converted in the partial oxidation, molecular oxygen and other inert diluent gases which are frequently also used in the partial oxidation, for example nitrogen and carbon dioxide. Depending on the separation process employed, steam may be present in the residual gas only in traces or in amounts of up to 20% by volume or more.

According to the invention, at least a portion (preferably the entire amount, if appropriate however only half, or two thirds, or three quarters, of this entire amount), (preferably having residual gas composition) comprising propane, molecular oxygen and any unconverted propylene, of this main residual gas is recycled as cycle gas 1 into reaction zone A. However, portions of residual gas may also be recycled into one or into both stages of the partial oxidation and/or be incinerated for the purpose of energy generation.

Of course, it is also possible, as described in this document and in EP-A 117 146, U.S. Pat. No. 3,161,670, DE-A 33 13 573 and DE-A 103 16 039, prior to use of residual gas as cycle gas 1, to partly or fully remove especially constituents other than propane, propylene and molecular oxygen from the residual gas. The latter is appropriate especially when product gas mixture A is used additionally in the process according to the invention to charge the at least one oxidation reactor.

In the workup of the condensed phase (for the purpose of removing the target product), further residual gases may occur, since it will normally be attempted to recycle the total amount of unconverted propane present in product gas mixture B into reaction zone A and to recover it in the target product removal. Although they generally still comprise propane and in some cases propylene, they frequently no longer comprise any molecular oxygen. Typically, they are recycled, combined with the main residual gas to give an overall residual gas, as cycle gas 1 into reaction zone A. However, it is also possible to separately utilize such further residual gases or to recycle them into reaction zone A.

The preferably full recycling of the overall residual gas thus allows continuous conversion of propane to acrylic acid and/or acrolein in continuous operation.

In this context, it is important that the recycling described and the inventive operating mode of reaction zone A make it possible to achieve therein a conversion of fresh propane to propylene with virtually one hundred percent selectivity.

The advantageousness of such a procedure exists both at lower (≦30 mol %) and at high (≧30 mol %) dehydrogenation conversions (based on single pass through reaction zone A). Generally, it is favorable in the case of the invention when the hydrogen content in the reaction gas mixture input stream into reaction zone A is in an at least stoichiometric ratio (based on oxygen combustion to water) to the amount of oxygen present therein.

It should also be emphasized once again here that acrylic acid is removed from a product gas mixture B obtained in accordance with the invention preferably in such a way that the product gas mixture B which has been cooled beforehand if appropriate by direct and/or indirect cooling is fractionally condensed, ascending (for example into itself), in a column comprising separating internals with side draw removal of crude acrylic acid, and/or absorbed by means of water and/or aqueous solution, as described by way of example in WO 2004/035 514 and DE-A 102 43 625. The crude acrylic acid withdrawn is subsequently preferably subjected to a suspension crystallization and the acrylic acid suspension crystals which are formed are preferably removed from remaining mother liquor by means of a wash column. Advantageously, the wash liquid used is the melt of acrylic acid crystals which have been removed beforehand in the wash column. Furthermore, the wash column is preferably one having forced transport of the crystal bed. It is more preferably a hydraulic or a mechanical wash column. For specific details, the description of WO 01/77 056, WO 03/041 832 and WO 03/041 833 may be followed. In other words, preference is given to recycling mother liquor which remains into the fractional condensation (cf. also EP-A 1 015 410). The secondary component discharge is normally below the side draw of the crude acrylic acid as a purge stream.

Using only one crystallization stage, it is thus possible to obtain acrylic acid having a purity of >99.8% by weight which is outstandingly suitable for producing superabsorbents based on poly-Na acrylate.

EXAMPLES

Construction Material: Type 1.4841 Stainless Steel

Example 1

DETAIL DESCRIPTION OF DRAWING

I. General Experimental Setup of Reaction Zone A and its Operating Mode

The heterogeneously catalyzed partial propane dehydrogenation is carried out in a tray loop reactor according to FIG. 1, to which the numerical addresses below relate.

A vertical tubular reactor (11) (internal diameter: 80 mm) is encased in a support heater (9) (enables substantial adiabaticity of the tubular reactor), provided with thermal insulation (10). The temperature of the support heater is 500° C. In the center of the tubular reactor is disposed a central tube (external diameter: 20 mm) which comprises a sleeve for a continuous thermoelement and a sleeve for a staged thermoelement. In addition, it comprises lines leading into the tubular reactor, through which reaction gas samples can be taken from the tubular reactor, and lines leading into the tubular reactor, through which air can be injected into the tubular reactor.

The tubular reactor comprises three trays (5, 6, 7) which consist of three identical beds of inert material (bed height: 100 mm; steatite spheres of diameter from 1.5 to 2.5 mm) and of a mixture (bed height: 165 mm) of dehydrogenation catalyst and steatite spheres (diameter from 1.5 to 2.5 mm) in a bed volume ratio of 1:1 (arranged in flow direction in the sequence specified) placed on a stainless steel wire mesh. The total bed height is thus in each case 265 mm.

The dehydrogenation catalyst is a Pt/Sn alloy which has been promoted with the elements Cs, K and La in oxidic form and which has been applied to the outer and inner surface of $ZrO_2 \cdot SiO_2$ mixed oxide support extrudates (mean length Gaussian distribution in the range from 3 to 12 mm with maximum at approx. 6 mm): 6 mm, diameter: 2 mm) in the elemental stoichiometry (mass ratios including support) of $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in Example 4 of DE-A 10219879).

Upstream of each catalyst tray is mounted a mixing element.

The product gas mixture A leaving the last tray (12) is divided into two halves of identical composition. One half (2) is recycled as product gas mixture A substream 1 (cycle gas 2) into the dehydrogenation as a constituent of the reaction gas mixture input stream for reaction zone A (4). The other half (1) is conducted as product gas mixture A substream 2 out of the dehydrogenation zone (reaction zone A).

Reaction gas mixture input stream (4) consists of product gas mixture A substream 1 (also known as cycle gas 2) (2) and of a gaseous starting mixture stream (3) which is composed of steam, cycle gas 1 from the partial oxidation, fresh propane and molecular hydrogen. This starting mixture stream (3) is the motive jet of a jet pump (it comprises a motive nozzle, a mixing zone, a diffuser and a suction nozzle, the conveying direction of the motive jet decompressed through the motive nozzle via the mixing zone and the diffuser pointing into the inlet of the reaction zone A and the suction direction of the suction nozzle in the direction of the outlet conducting product gas mixture stream A of the reaction zone A, and the reduced pressure generated in the suction nozzle, with division of product gas mixture stream A into the two substreams 1 and 2, sucks in product gas mixture A substream 1 and transports it through the mixing zone via the diffuser with simultaneous mixing with the motive jet, and the reaction gas mixture input stream formed in this way is released into the inlet of the reaction zone A) which divides product gas mixture stream A (12) as described and generates the reaction gas mixture input stream for reaction zone A (4).

The loading of the total amount of catalyst (calculated without inert material) on all trays with propane is always 350 l (STP)/l·h.

The entrance pressure of the reaction gas mixture input stream for reaction zone A is 2.3 bar. Its temperature is 500° C. The pressure drop over the dehydrogenation reactor is approx. 200 mbar. Upstream of (in each case before the mixing element) the second and upstream of the third catalyst bed (in flow direction), air (500° C., reaction pressure) is injected into the reaction gas mixture. The amount is such that the highest temperature in the downstream catalyst bed in each case is from 575 to 580° C.

II. General Experimental Setup of the Heterogeneously Catalyzed Two-Stage Partial Oxidation of Propylene to Acrylic Acid and its Operating Mode Experimental Arrangement First Reaction Stage:

A reaction tube (V2A steel; external diameter 30 mm, wall thickness 2 mm, internal diameter 28 mm, length: 350 cm, and also a thermal tube (external diameter 10 mm), centered in the middle of the reaction tube, to accommodate a thermoelement with which the temperature in the reaction tube can be determined for its entire length) is charged from top to bottom as follows:

Section 1: Length 50 cm
  Steatite rings of geometry 7 mm×7 mm×4 mm (external diameter×length×internal diameter) as a preliminary bed.

Section 2: Length 140 cm
  Catalyst charge of a homogeneous mixture of 20% by weight (alternatively 30% by weight) of steatite rings of geometry 5 mm×3 mm×2 mm (external diameter× lengthxinternal diameter) and 80% by weight (alternatively 70% by weight) of unsupported catalyst from section 3.

Section 3: Length 160 cm

Catalyst charge of annular (5 mm×3 mm×2 mm=external diameter×length×internal diameter) unsupported catalyst according to Example 1 of DE-A 10046957 (stoichiometry: $[Bi_2W_2O_9.2WO_3]_{0.5}[Mo_{12}Co_{5.5}Fe_{2.94}Si_{1.59}K_{0.08}O_x]_1$). Alternatively, it is also possible here to use one of the catalysts EUC1 to EUC11 from Research Disclosure No. 497012 of Aug. 29, 2005.

From top to bottom, the first 175 cm are thermostated by means of a salt bath A pumped in countercurrent (to the reaction gas). The second 175 cm are thermostated by means of a salt bath B pumped in countercurrent (to the reaction gas).

Second Reaction Stage:

A reaction tube (V2A steel; external diameter 30 mm, wall thickness 2 mm, internal diameter 28 mm, length: 350 cm, and also a thermal tube (external diameter 10 mm), centered in the middle of the reaction tube, to accommodate a thermoelement with which the temperature in the reaction tube can be determined for its entire length) is charged from top to bottom as follows:

Section 1: Length 20 cm

Steatite rings of geometry 7 mm×7 mm×4 mm (external diameter×length×internal diameter) as a preliminary bed.

Section 2: Length 90 cm

Catalyst charge of a homogeneous mixture of 25% by weight (alternatively 30% by weight) of steatite rings of geometry 7 mm×3 mm×4 mm (external diameter x length x internal diameter) and 75% by weight (alternatively 70% by weight) of coated catalyst from section 4.

Section 3: Length 50 cm

Catalyst charge of a homogeneous mixture of 15% by weight (alternatively 20% by weight) of steatite rings of geometry 7 mm×3 mm×4 mm (external diameter× length×internal diameter) and 85% by weight (alternatively 80% by weight) of coated catalyst from section 4.

Section 4: Length 190 cm

Catalyst charge of annular (7 mm×3 mm×4 mm=external diameter×length×internal diameter) coated catalyst according to Preparation Example 5 of DE-A 10046928 (stoichiometry: $Mo_{12}V_3W_{1.2}Cu_{2.4}O_x$).

From top to bottom, the first 175 cm are thermostated by means of a salt bath C pumped in countercurrent (to the reaction gas). The second 175 cm are thermostated by means of a salt bath D pumped in countercurrent.

III. Process for Preparing Acrylic Acid from Propane (the Steady Operating State is Described)

A reaction gas mixture input stream which has the following contents (% by volume based on overall gas) is fed to the first catalyst bed of a tray reactor as described in I:

|  | % by volume |
| --- | --- |
| acrylic acid | 0.01 |
| acetic acid | 0.015 |
| water | 9.23 |
| 1-butene | 0.01 |
| isobutene | 0.02 |
| propane | 18.46 |
| propylene | 3.98 |
| ethane | 1.16 |

-continued

|  | % by volume |
| --- | --- |
| ethylene | 0.22 |
| $CO_2$ | 2.34 |
| CO | 0.26 |
| $N_2$ | 59.7 |
| $O_2$ | 1.62 |
| $CH_4$ | 0.12 |
| $H_2$ | 2.83 |

It is obtained (it comprises) from (in the sequence of cycle gas 1 (23° C., 3.1 bar), fresh propane (25° C., 4 bar), steam (200° C., 2.5 bar), hydrogen (25° C., 8 bar), dehydrogenation cycle gas (cycle gas 2) (600° C., 1.9 bar)):

41.9% by volume of residual gas from the partial oxidation (cycle gas 1) which has the following contents:

|  | % by volume |
| --- | --- |
| acrylic acid | 0.02 |
| acetic acid | 0.04 |
| $H_2O$ | 2.73 |
| isobutene | 0.01 |
| acrolein | 0.05 |
| propane | 17.30 |
| propylene | 0.32 |
| ethane | 1.20 |
| ethylene | 0.22 |
| $CO_2$ | 2.41 |
| CO | 0.61 |
| $N_2$ | 71.21 |
| $O_2$ | 3.87 |

3.9% by volume of fresh propane which has the following contents:

|  | % by volume |
| --- | --- |
| propane | 98.91 |
| isobutane | 0.05 |
| propylene | 0.1 |
| ethane | 0.92 |
| ethylene | 0.01 |

1.02% by volume of molecular hydrogen 2.03% by volume of steam and 51.15% by volume of dehydrogenation cycle gas (product gas mixture A substream 1 or cycle gas 2)

Residual gas (cycle gas 1), fresh propane, steam and hydrogen are combined in the sequence specified to give the motive jet mixture stream and brought to 500° C., 2.3 bar by indirect heat exchange with product gas mixture A substream 2.

The resulting product gas mixture A substream 2 has the following contents:

|  | % by volume |
| --- | --- |
| $H_2O$ | 11.84 |
| isobutene | 0.01 |
| propane | 14.32 |
| propylene | 7.52 |
| ethane | 1.21 |
| ethylene | 0.26 |
| $CO_2$ | 2.61 |

-continued

| | % by volume |
|---|---|
| $N_2$ | 58.41 |
| $O_2$ | 0.23 |
| $H_2$ | 3.55 |

The propane and propylene present in product gas mixture A substream 2 is removed absorptively by absorption in PKWF 4/7 af technical-grade tetradecane from Haltermann, Germany as the absorbent (alternatively, it is also possible here to use LINPAR 14-17 from CONDEA Augusta S.p.A. (Italy)), and stripped by means of air to free it therefrom (the procedure is as described in DE-A 10 2004 032 129) to obtain the following charge gas for the partial oxidation which has the following contents:

| | % by volume |
|---|---|
| $H_2O$ | 2.39 |
| tetradecane | 0.01 |
| isobutene | 0.01 |
| propane | 15.15 |
| propylene | 7.95 |
| ethane | 1.10 |
| ethylene | 0.20 |
| $CO_2$ | 1.05 |
| $N_2$ | 56.99 |
| $O_2$ | 15.16 |

This charge gas mixture (it lies outside the explosion range) is used to charge the first partial oxidation reaction stage described. The propylene loading on the fixed bed catalyst charge is selected at 185 l (STP)/l·h. The pressure at the entrance to the first reaction stage is 3.1 bar. $T_A$=322° C.; $T_B$=328° C.

The product gas mixture leaving the first reaction stage has the following contents:

| | % by volume |
|---|---|
| acrylic acid | 0.46 |
| acetic acid | 0.14 |
| $H_2O$ | 10.65 |
| 1-butene | 0.01 |
| acrolein | 6.99 |
| propane | 15.16 |
| propylene | 0.17 |
| ethane | 1.10 |
| ethylene | 0.20 |
| $CO_2$ | 1.62 |
| CO | 0.23 |
| $N_2$ | 57.02 |
| $O_2$ | 6.25 |

$C^P_A$, the propene conversion at the end of reaction zone A, is 64.5 mol %.

$C^P_B$, the propene conversion at the end of reaction zone B, is 94.9 mol %.

Sufficient air (25° C.) is metered to the product gas mixture of the first stage that the molar $O_2$:acrolein ratio in the resulting mixture is 1.25.

This mixture is then used directly to charge the second reaction stage (T=231.7° C.). The acrolein loading on the fixed catalyst bed is 152 l (STP)/l·h. $T_C$=263° C.; $T_D$=269° C. The pressure at the entrance to the second reaction stage is 2.1 bar.

The product gas mixture B leaving the second reaction stage has the following contents:

| | % by volume |
|---|---|
| acrylic acid | 6.72 |
| acetic acid | 0.22 |
| $H_2O$ | 11.06 |
| formaldehyde | 0.14 |
| acrolein | 0.05 |
| formic acid | 0.03 |
| maleic anhydride | 0.06 |
| benzene acid | 0.01 |
| propane | 14.62 |
| propylene | 0.28 |
| ethane | 1.02 |
| ethylene | 0.18 |
| $CO_2$ | 2.03 |
| CO | 0.52 |
| $N_2$ | 59.86 |
| $O_2$ | 3.20 |
| propionic acid | 0.0032 |

$C^A_C$, the acrolein conversion at the end of reaction zone C, is 68.1 mol %.

$C^A_D$, the acrolein conversion at the end of reaction zone D, is 99.3 mol %.

In both reaction stages, the reaction gas mixture flows through the two catalyst tubes from the top downward.

The contents are analyzed by means of gas chromatography analysis.

The acrylic acid is removed from the product gas mixture as in the exemplary embodiments of DE-A 10 2004 032 129 and the residual gas comprising the molecular oxygen is recycled into the heterogeneously catalyzed dehydrogenation as the cycle gas 1.

The process may also be carried out as described, but with the difference that each catalyst tray in reaction zone A is only charged with the same amount of dehydrogenation catalyst, i.e. without additional use of inert material for dilution purposes.

The steady operating state described is disrupted for the duration of 2 minutes by increasing the amount of air metered into the product gas mixture of the first partial oxidation stage to such an extent that the content of $O_2$ in product gas mixture B rises initially to 3.40% by volume.

The residual oxygen content of 3.20% by volume in product gas mixture B can be restored and subsequently maintained during the 2-minute disruption to operation by increasing the amount of fresh propane to the reaction gas mixture input stream for reaction zone A under otherwise unchanged conditions by from 1/100 to 3/100 (based on the initial value). The reaction temperature in reaction zone A is substantially retained (unchanged).

With application of the inventive regulation principle, long-term steady-state operation is possible, which always deviates only slightly from the ideal line.

Example 2

I. General Experimental Setup of Reaction Zone A and its Operating Mode.

The heterogeneously catalyzed partial propane dehydrogenation is carried out in straight pass (i.e. without loop mode) in a tray reactor described below. A vertical tubular reactor (internal diameter: 80 mm) is encased in a support heater (enables substantial adiabaticity of the tubular reactor), provided with thermal insulation. The temperature of the support heater is 500° C. In the center of the tubular reactor is disposed a central tube (external diameter: 20 mm) which comprises a sleeve for a continuous thermoelement and a sleeve for a staged thermoelement. In addition, it comprises lines leading into the tubular reactor, through which reaction gas samples can be taken from the tubular reactor, and lines leading into the tubular reactor, through which air can be injected into the tubular reactor.

The tubular reactor comprises three trays arranged in succession, which consist of three identical beds placed on a stainless steel wire mesh (arranged in the sequence specified in flow direction) of inert material (bed height: 26 mm; steatite spheres of diameter 1.5 to 2.5 mm) and a mixture (bed height: 174 mm) of dehydrogenation catalyst and steatite spheres (diameter 1.5 to 2.5 mm) in a bed volume ratio of 1:3. The total bed height is thus in each case 200 mm. The dehydrogenation catalyst used is the dehydrogenation catalyst from example 1. Upstream of each catalyst tray is disposed a mixing element.

The loading on the total amount of catalyst (calculated without inert material) of all trays with propane is 1500 l (STP)/l·h.

The entrance pressure of the reaction gas mixture input stream for reaction zone A is 3.1 bar. Its temperature is 450° C. The pressure drop over the dehydrogenation reactor is approx. 400 mbar. Before (in each case before the mixing element) of the second catalyst bed and before the third catalyst bed (in flow direction), air (500° C., reaction pressure) is injected to the reaction mixture. The amount is such that the highest temperature in the downstream catalyst bed in each case is from 575 to 580° C.

II. General Experimental Setup of the Heterogeneously Catalyzed Two-Stage Partial Oxidation of Propylene to Acrylic Acid and its Operating Mode As in example 1.

III. Process for Preparing Acrylic Acid from Propane (the Steady Operating State is Described)

A reaction gas mixture input stream which has the following contents is fed to the first catalyst bed of the tray reactor as described in I. (% by volume based on total gas):

|  | % by vol. |
|---|---|
| acrylic acid | 0.033 |
| acetic acid | 0.017 |
| water | 9.23 |
| n-butane | 0.0004 |
| isobutane | 0.008 |
| formic acid | 0.0005 |
| acrolein | 0.024 |
| propionic acid | 0.0001 |
| methacrylic acid | 0.0001 |
| furfural | 0.0001 |
| propane | 32.93 |
| propylene | 0.19 |
| ethylene | 0.035 |
| ethane | 0.18 |
| $N_2$ | 51.33 |
| $O_2$ | 2.97 |
| $CO_2$ | 1.7 |
| $H_2$ | 0.09 |
| CO | 0.38 |

It is obtained (it comprises) from (in the sequence of cycle gas 1 (23° C., 3.1 bar), fresh propane (25° C., 4 bar), steam (200° C., 2.5 bar)):

86.61% by volume of residual gas from the partial oxidation (cycle gas 1) which has the following contents:

|  | % by vol. |
|---|---|
| acrylic acid | 0.038 |
| acetic acid | 0.020 |
| $H_2O$ | 2.99 |
| n-butane | 0.0004 |
| isobutane | 0.0052 |
| formic acid | 0.0006 |
| acrolein | 0.028 |
| propionic acid | 0.0001 |
| furfural | 0.0001 |
| propane | 30.4 |
| propylene | 0.21 |
| ethylene | 0.037 |
| ethane | 0.14 |
| $N_2$ | 59.32 |
| $O_2$ | 3.43 |
| $CO_2$ | 1.98 |
| $H_2$ | 0.1 |
| CO | 0.44 |

6.75% by volume of fresh propane which has the following contents:

|  | % by vol. |
|---|---|
| n-butane | 0.0007 |
| isobutane | 0.045 |
| propane | 98 |
| propylene | 0.11 |
| ethylene | 0.014 |
| ethane | 0.92 | and 6.64% by volume of steam.

Residual gas (cycle gas 1), fresh propane and steam are combined in the sequence specified and brought to 450° C., 3.1 bar by indirect heat exchange with product gas mixture A or by means of electric heating.

The resulting product gas mixture A has the following contents (data in % by volume):

|  | % by vol. |
|---|---|
| $H_2O$ | 0.845 |
| n-butane | 0.0003 |
| isobutane | 0.0051 |
| 1-butene | 0.0001 |
| isobutene | 0.0022 |
| propane | 29.07 |
| propylene | 6.84 |
| ethylene | 0.037 |
| ethane | 0.13 |
| $N_2$ | 48.72 |
| $O_2$ | 12.43 |
| $CO_2$ | 0.806 |
| $H_2$ | 0.1 |

The propane and propylene present in product gas mixture A is removed absorptively by absorption in PKWF 4/7 af technical-grade tetradecane from Haltermann, Germany as the absorbent (or alternatively, it is also possible here to use LINPAR 14-17 from CONDEA Augusta S.p.A. (Italy)), and stripped by means of air to free it therefrom (the procedure is as described in DE-A 10 2004 032 129) to obtain the following charge gas for the partial oxidation which has the following contents (data in % by volume):

|  | % by vol. |
|---|---|
| $H_2O$ | 2.5 |
| tetradecane | 0.006 |
| n-butane | 0.0003 |
| isobutane | 0.0051 |
| 1-butene | 0.0001 |
| isobutene | 0.0022 |
| propane | 28.57 |
| propylene | 6.73 |
| ethylene | 0.037 |
| ethane | 0.13 |
| $N_2$ | 47.9 |
| $O_2$ | 12.22 |
| $CO_2$ | 0.88 |
| $H_2$ | 0.097 |

This charge gas mixture (it lies outside the explosion range) is used to charge the first partial oxidation stage described. The propylene loading on the fixed catalyst bed charge is selected at 145 *(STP)/l·h*. *The pressure at the entrance to the first reaction stage is* 3.1 bar. $T_A$=324° C.; $T_B$=328° C.

The product gas mixture leaving the first reaction stage has the following contents (data in % by volume):

|  | % by vol. |
|---|---|
| acrylic acid | 0.33 |
| acetic acid | 0.026 |
| steam | 9.28 |
| n-butane | 0.0003 |
| isobutane | 0.0051 |
| acrolein | 5.90 |
| propionic acid | 0 |
| methacrylic acid | 0.0002 |
| propane | 28.52 |
| propylene | 0.38 |
| ethylene | 0.037 |
| ethane | 0.13 |
| $N_2$ | 47.89 |
| $O_2$ | 5.1 |
| $CO_2$ | 1.3 |
| CO | 0.18 |

$C^P_A$, the propene conversion at the end of reaction zone A, is 64.5 mol %.

$C^P_B$, the propene conversion at the end of reaction zone B, is 94.9 mol %.

Sufficient air (25° C.) is metered into the product mixture of the first stage that the molar $O_2$: acrolein ratio in the resulting mixture is 1.22.

This mixture is then used directly to charge the second reaction stage (T=231.7° C.).

The acrolein loading on the fixed catalyst bed is 121 l (STP)/l·h.

$T_C$=265° C.; $T_D$=269° C. The pressure at the entrance to the second reaction stage is 2.1 bar.

The product gas mixture B leaving the second reaction stage has the following contents (data in % by volume):

|  | % by vol. |
|---|---|
| acrylic acid | 5.52 |
| acetic acid | 0.11 |
| $H_2O$ | 9.44 |
| n-butane | 0.0003 |
| isobutane | 0.0047 |
| formic acid | 0.0063 |
| formaldehyde | 0.044 |
| acrolein | 0.025 |
| propionic acid | 0.0029 |
| methacrylic acid | 0.0002 |
| furfural | 0.0017 |
| benzaldehyde | 0.0008 |
| maleic anhydride | 0.043 |
| propane | 26.47 |
| propylene | 0.19 |
| ethylene | 0.034 |
| ethane | 0.12 |
| $N_2$ | 51.89 |
| $O_2$ | 3 |
| $CO_2$ | 1.6 |
| $H_2$ | 0.09 |
| CO | 0.39 |

$C^A_C$, the acrolein conversion at the end of reaction zone C, is 68.1 mol %.

$C^A_D$, the acrolein conversion at the end of reaction zone D, is 99.2 mol %.

In both reaction stages, the reaction gas mixture flows through the two catalyst tubes from the top downward.

The contents are analyzed by means of gas chromatography analysis.

The acrylic acid is removed from the product gas mixture as in the exemplary embodiments of DE-A 10 2004 032 129 and the residual gas comprising molecular oxygen is recycled as cycle gas 1 into the heterogeneously catalyzed dehydrogenation.

The process may also be carried out as described, but with the difference that each catalyst tray in reaction zone A is only charged with the same amount of dehydrogenation catalyst, i.e. without additional use of inert material for dilution purposes.

The steady operating state described is disrupted for the duration of 2 minutes by reducing the amount of air metered into the product gas mixture of the first partial oxidation stage to such an extent that the content of $O_2$ in product gas mixture B falls initially to 2.80% by volume.

The residual oxygen content of 3.20% by volume in product gas mixture B can be restored and subsequently maintained during the 2-minute disruption to operation by lowering the amount of fresh propane to the reaction gas mixture input stream for reaction zone A under otherwise unchanged conditions by from 1/100 to 3/100 (based on the initial value). The reaction temperature in reaction zone A is substantially retained (unchanged).

With application of the inventive regulation principle, long-term steady-state operation is possible, which always deviates only slightly from the ideal line.

U.S. Provisional Patent Application No. 60/732,658, filed on Nov. 3, 2005, is incorporated into the present patent application by literature reference.

With regard to the abovementioned teachings, numerous changes and deviations from the present invention are possible.

It can therefore be assumed that the invention, within the scope of the appended claims, can be performed differently from the way described specifically herein.

What is claimed is:

1. A process for stably operating a continuous preparation process for obtaining acrolein or acrylic acid or a mixture thereof from propane, in which
   A) in a first reaction zone A, propane is subjected in the presence of molecular oxygen to a heterogeneously catalyzed dehydrogenation to obtain a product gas mixture A comprising propane and propylene,
   B) if appropriate, product gas mixture A is conducted into a first separation zone A in order to remove a portion or more of constituents other than propane and propylene present in product gas mixture A therefrom and thus to obtain a remaining product gas mixture A' comprising propane and propylene,
   C) product gas mixture A or product gas mixture A' is used in a second reaction zone B to charge at least one oxidation reactor and, in the at least one oxidation reactor, propylene present in product gas mixture A or in product gas mixture A' is subjected to a selective heterogeneously catalyzed partial gas phase oxidation with molecular oxygen to give a product gas mixture B comprising acrolein or acrylic acid or a mixture thereof as the target product, unconverted propane, excess molecular oxygen and any unconverted propylene,
   D) in a second separation zone B, target product present in product gas mixture B is removed and, from the remaining residual gas comprising propane, molecular oxygen and any unconverted propylene, at least a portion comprising unconverted propane, molecular oxygen and any unconverted propylene is recycled as cycle gas 1 comprising molecular oxygen into reaction zone A in cycle gas mode,
   E) fresh propane is fed to the continuous preparation process via at least one of the zones from the group comprising reaction zone A, separation zone A, reaction zone B and separation zone B at a feed rate which has a predefined steady-state value in the stable operating state of the preparation process, and
   F) the content of molecular oxygen in product gas mixture B is determined continuously and compared to the steady-state target content of molecular oxygen in product gas mixture B predefined for the stable operating state of the preparation process,
   wherein
   in the case that the content of molecular oxygen determined at one time in product gas mixture B is greater than the steady-state target content, after this time, fresh propane is fed to the preparation process at a feed rate which is greater than its steady-state value, and
   in the case that the content of molecular oxygen determined at one time in product gas mixture B is less than the steady-state target content, after this time, fresh propane is fed to the preparation process at a feed rate which is less than its steady-state value.

2. The process according to claim 1, wherein the continuous determination of the content of molecular oxygen in product gas mixture B is based on obtaining a signal which is correlated to the oxygen content of product gas mixture B.

3. The process according to claim 2, wherein the signal is obtained by passing electromagnetic radiation having a wavelength at which molecular oxygen absorbs electromagnetic radiation through product gas mixture B and measuring the unabsorbed fraction of the electromagnetic radiation.

4. The process according to claim 3, wherein the wavelength is from 759.5 nm to 768 nm.

5. The process according to claim 2, wherein the determination of the content of molecular oxygen in product gas mixture B is based on the comparatively great paramagnetic susceptibility of molecular oxygen.

6. The process according to any of claims 1 to 5, wherein the steady-state target content of molecular oxygen in product gas mixture B is from 0.1 to 6% by volume.

7. The process according to any of claims 1 to 5, wherein the steady-state target content of molecular oxygen in product gas mixture B is from 0.5 to 5% by volume.

8. The process according to any of claims 1 to 5, wherein the steady-state target content of molecular oxygen in product gas mixture B is from 0.1 to 6% by weight.

9. The process according to any of claims 1 to 5, wherein the steady-state target content of molecular oxygen in product gas mixture B is from 0.5 to 5% by weight.

10. The process according to claim 1, wherein fresh propane is fed only via reaction zone A.

11. The process according to claim 1, wherein the heterogeneously catalyzed dehydrogenation in reaction zone A is carried out in a tray reactor.

12. The process according to claim 1, wherein the heterogeneously catalyzed dehydrogenation in reaction zone A is operated adiabatically.

13. The process according to claim 1, wherein the heterogeneous y catalyzed dehydrogenation in reaction zone A is performed autothermally.

14. The process according to claim 1, wherein the feed rate of fresh propane is charged directly into reaction zone A.

* * * * *